US007972600B2

(12) United States Patent
Ludwig et al.

(10) Patent No.: US 7,972,600 B2
(45) Date of Patent: Jul. 5, 2011

(54) IGF-IR ANTAGONISTS AS ADJUVANTS FOR TREATMENT OF PROSTATE CANCER

(75) Inventors: Dale L. Ludwig, Randolph, NJ (US); Stephen R. Plymate, Des Moines, WA (US)

(73) Assignees: ImClone LLC, New York, NY (US); University of Washington, Seattle, WA (US)

( * ) Notice: Subject to any disclaimer, the term of this patent is extended or adjusted under 35 U.S.C. 154(b) by 1054 days.

(21) Appl. No.: 11/702,838

(22) Filed: Feb. 5, 2007

(65) Prior Publication Data

US 2009/0175868 A1 Jul. 9, 2009

Related U.S. Application Data

(60) Provisional application No. 60/765,072, filed on Feb. 3, 2006.

(51) Int. Cl.
*A61K 39/395* (2006.01)
*A61K 47/48* (2006.01)
*A61K 31/517* (2006.01)
*C07K 16/00* (2006.01)
*C07K 16/28* (2006.01)

(52) U.S. Cl. ............... 424/155.1; 424/143.1; 514/266.2; 514/266.21; 530/387.9; 530/388.22; 544/284

(58) Field of Classification Search ............. 435/6, 91.1, 435/455; 514/1, 2, 44, 266.2, 266.21; 530/300, 530/350, 387.1, 388.1, 388.24, 387.9, 388.22; 424/143.1, 155.1; 544/284
See application file for complete search history.

(56) References Cited

U.S. PATENT DOCUMENTS

| | | | |
|---|---|---|---|
| 4,774,321 A | 9/1988 | Rosner et al. | |
| 5,200,509 A | 4/1993 | Spencer et al. | |
| 5,262,308 A | 11/1993 | Baserga | |
| 5,597,563 A | 1/1997 | Beschorner | |
| 5,624,805 A | 4/1997 | Spencer et al. | |
| 5,670,341 A | 9/1997 | Spencer et al. | |
| 5,681,818 A | 10/1997 | Spencer et al. | |
| 5,688,505 A | 11/1997 | Webb et al. | |
| 5,705,157 A | 1/1998 | Greene | |
| 5,798,266 A | 8/1998 | Quay et al. | |
| 5,852,174 A | 12/1998 | Vlassara et al. | |
| 5,869,337 A | 2/1999 | Crabtree et al. | |
| 5,872,220 A | 2/1999 | Kiefer et al. | |
| 5,891,722 A | 4/1999 | Fuks et al. | |
| 5,939,269 A | 8/1999 | Goldfine et al. | |
| 5,942,412 A | 8/1999 | Prager et al. | |
| 5,968,508 A | 10/1999 | Goldfine | |
| 5,968,758 A | 10/1999 | Fuks et al. | |
| 5,977,307 A | 11/1999 | Friden et al. | |
| 5,993,818 A | 11/1999 | Torchilin et al. | |
| 6,071,891 A | 6/2000 | Low et al. | |
| 6,084,085 A | 7/2000 | Baserga et al. | |
| 6,090,383 A | 7/2000 | Dasch et al. | |
| 6,316,462 B1 | 11/2001 | Bishop et al. | |
| 6,368,826 B1 | 4/2002 | Ligensa et al. | |
| 6,875,741 B2 | 4/2005 | Pillutla et al. | |
| 7,037,498 B2 | 5/2006 | Cohen et al. | |
| 7,071,160 B2 | 7/2006 | Yamano et al. | |
| 7,071,300 B2 | 7/2006 | Deshayes et al. | |
| 7,217,796 B2 | 5/2007 | Wang et al. | |
| 7,241,444 B2 | 7/2007 | Goetsch et al. | |
| 7,300,655 B2 | 11/2007 | Hansen et al. | |
| 7,329,745 B2 | 2/2008 | Fujita-Yamaguchi | |
| 7,371,378 B2 | 5/2008 | Cohen et al. | |
| 7,432,244 B2 | 10/2008 | Deshayes et al. | |
| 7,598,350 B2 * | 10/2009 | Liu et al. ................... 530/387.9 |
| 7,638,605 B2 | 12/2009 | Ludwig | |
| 2003/0021780 A1 | 1/2003 | Smith et al. | |
| 2003/0165502 A1 | 9/2003 | Fujita-Yamaguchi | |
| 2003/0235582 A1 | 12/2003 | Singh et al. | |
| 2004/0018191 A1 | 1/2004 | Wang et al. | |
| 2004/0057950 A1 | 3/2004 | Waksal et al. | |
| 2004/0102360 A1 | 5/2004 | Barnett et al. | |
| 2004/0116330 A1 | 6/2004 | Naito et al. | |
| 2004/0141958 A1 | 7/2004 | Steinaa et al. | |
| 2004/0202651 A1 | 10/2004 | Cohen et al. | |
| 2004/0202655 A1 | 10/2004 | Morton et al. | |
| 2004/0214898 A1 * | 10/2004 | Steiner et al. ................. 514/651 |
| 2004/0228859 A1 | 11/2004 | Graus et al. | |
| 2004/0265307 A1 | 12/2004 | Singh et al. | |
| 2005/0008642 A1 | 1/2005 | Graus et al. | |
| 2005/0079184 A1 | 4/2005 | Hsing-Chang et al. | |
| 2005/0084906 A1 | 4/2005 | Goetsch et al. | |
| 2005/0136063 A1 | 6/2005 | Wang et al. | |
| 2005/0164970 A1 | 7/2005 | Li | |
| 2005/0186203 A1 | 8/2005 | Singh et al. | |
| 2005/0244408 A1 | 11/2005 | Cohen et al. | |
| 2005/0249728 A1 | 11/2005 | Singh et al. | |
| 2005/0249730 A1 * | 11/2005 | Goetsch et al. ............. 424/143.1 |
| 2005/0281812 A1 | 12/2005 | Cohen et al. | |
| 2006/0088539 A1 * | 4/2006 | Bander ....................... 424/155.1 |
| 2006/0106203 A1 | 5/2006 | Winter et al. | |
| 2006/0134172 A1 | 6/2006 | Shepard et al. | |

(Continued)

FOREIGN PATENT DOCUMENTS

EP  0294021  12/1988

(Continued)

OTHER PUBLICATIONS

Hellawell, et al., Cancer Research 6:2942-2950 (2002).

(Continued)

*Primary Examiner* — Jane Zara
(74) *Attorney, Agent, or Firm* — Nicole S. Woods; Sanjay Jivraj

(57) ABSTRACT

The present invention relates to a method of treating prostate cancer with androgen deprivation therapy and an insulin-like growth factor receptor (IGF-IR) antagonist. Although the response rate of prostate cancer to androgen deprivation therapy (ADT) is high, surviving cancer cells invariably become androgen independent (AI) and tumor growth follows. The invention inhibits or delays transition of androgen dependent cancer to androgen independent cancer, significantly decreases risk of recurrence, and improves treatment outcome.

13 Claims, 7 Drawing Sheets

U.S. PATENT DOCUMENTS

| | | | |
|---|---|---|---|
| 2006/0149033 A1 | 7/2006 | Deshayes et al. | |
| 2006/0193772 A1 | 8/2006 | Ochiai et al. | |
| 2006/0233814 A1 | 10/2006 | Goldmakher et al. | |
| 2007/0009970 A1 | 1/2007 | Heller et al. | |
| 2007/0010537 A1* | 1/2007 | Hamamura et al. | 514/266.2 |
| 2007/0196376 A1 | 8/2007 | Raeber et al. | |
| 2009/0110678 A1* | 4/2009 | Ludwig et al. | 424/133.1 |

FOREIGN PATENT DOCUMENTS

| | | |
|---|---|---|
| EP | 0369943 | 5/1990 |
| EP | 0375438 | 6/1990 |
| WO | 8906692 | 7/1989 |
| WO | 96/30347 | 10/1996 |
| WO | 96/40210 | 12/1996 |
| WO | 9744352 | 11/1997 |
| WO | 9825642 | 6/1998 |
| WO | 99/08668 | 2/1999 |
| WO | 01/90192 | 11/2001 |
| WO | 02053596 | 7/2002 |
| WO | 03059951 | 7/2003 |
| WO | 03100008 | 12/2003 |
| WO | 03106621 | 12/2003 |
| WO | 2004071529 | 8/2004 |
| WO | 2004083248 | 9/2004 |
| WO | 2004087756 | 10/2004 |
| WO | 2005005635 | 1/2005 |
| WO | 2005016970 | 2/2005 |
| WO | 2005052005 | 6/2005 |
| WO | 2005/090407 | 9/2005 |
| WO | 2005082415 | 9/2005 |
| WO | 2006008639 | 1/2006 |
| WO | 2006/020258 | 2/2006 |
| WO | 2006013472 | 2/2006 |
| WO | 2006060419 | 6/2006 |
| WO | 2006069202 | 6/2006 |
| WO | 2007000328 | 1/2007 |
| WO | 2007012614 | 2/2007 |
| WO | 2007031875 | 3/2007 |

OTHER PUBLICATIONS

Nickerson, et al., Cancer Research 61:6276-6280 (2001).
Burtrum, et al., Cancer Res. 63:8912-8921 (2003).
Corey, et al., Prostate 99:392-401 (2003).
Greenman, et al., Nature 446(8):153-158 (2007).
Li, et al., Can. Immunol. Immunother. 49:243-252 (2000).
Tennant, et al., Prostate 56:115-122 (2003).
Wu, et al., Clin. Cancer Res. 11:3065-3074 (2005).
Yu, et al., Natl. Cancer Inst. 92:1472-1489 (2000).
Adams, et al., Cell. Mol. Life Sci. 57:1050-1093 (2000).
Baserga, Oncogene 19:5574-5581 (2000).
Batley, et al., Life Sci. 62:143-150 (1998).
Bonifacino, et al., Current Protocols in Cell Biology, Wiley & Sons (1999).
Coligan, et al., Current Protocols in Immunology, Wiley & Sons, Inc. (1991).
Collins, Glia 15:289-296 (1995).
de Hoon, et al., Bioinformatics 20:1453-1454 (2004).
Elbashir, et al., Nature 411:494-498 (2001).
Enna, et al., Current Protocols in Pharmacology, Wiley & Sons (1991).
Freireich, et al., Cancer Chemother. Rep. 50(4):219-245 (1966).
Ganesan, Drug Discov. Today 7(1):47-55 (2002).
Garcia-Echeverria, et al., Cancer Cell 5:231-239 (2004).
Geller, et al., J. Urol. 132:693-700 (1984).
Girnita, et al., Cancer Res. 64:236-242 (2004).
Grandis, et al., Cancer 78:1284-1292 (1996).
Haluska, et al., Cancer Res. 66:362-371 (2006).
Hoffmann, et al., Anticancer Res. 17:4419-4426 (1997).
Khvorova, Cell 115:209-216 (2003).
Lou, Drug. Discov. Today 6(24):1288-1294 (2001).
Mello, et al., Nature 431:338-342 (2004).
Mitsiades, et al., Cancer Cell 5:221-230 (2004).
Moyer, et al., Cancer Res. 57:4838-4848 (1997).
Nelson, et al., Nucl. Acids Res. 30(1):218-220 (2002).
O'Connor, et al., Horm. Metub. Res. 35:771-777 (2003).
Paddison, et al., Curr. Opin. Mol. Ther. 5:217-224 (2003).
Page, Comput. Appl. Biosci., 12:357-358 (1996).
Pandini, et al., Clin. Can. Res. 5:1935-1944 (1999).
Panek, et al., J. Pharmacol. Exp. Thera. 283:1433-1444 (1997).
Parrizas, et al., Endocrinology 138(4):1427-1433 (1997).
Petrides, et al., Cancer Res. 50:3934-3939 (1990).
Pollack, et al., J. Pharmacol., 291:739-748 (1999).
Radinsky, et al., Clin. Cancer Res. 1:19-31 (1995).
Sambrook, et al., Molecular Cloning: A Laboratory Manual, 2nd ed., Cold Spring Harbor Laboratory Press (1989).
Sauter, et al., Am. J. Path., 148:1047-1053 (1996).
Sazani, et al., J. Clin. Invest. 112:481-486 (2003).
Shimizu, et al., Japan J. Cancer Res. 85:567-571 (1994).
Siddle, et al., The IGF System, Humana Press, pp. 199-225 (1999).
Tusher, et al., Proc. Natl. Acad. Sci. USA 98(9):5116-5121 (2001).
Wikstrand, et al., Cancer Res. 55:3140-3148 (1995).
Williams, Biochem. Soc. Trans. 25:509-513 (1997).
Wittman, et al., J. Med. Chem. 48:5639-5643 (2005).
Wraight, Nat. Biotechnol. 18:521-6 (2000).
Wu, et al., Clin. Cancer Res. 12(20):6153-6160 (2006).
Zamecnik, et al., Proc. Natl. Acad. Sci. USA 75(1):280-284 (1978).
Zhang, et al., Oncogene 24:2474-2482 (2005).
Burfeind, et al., PNAS 93(14):7263-7268 (1996).
Hofmann, et al., Drug Disc. Today 10(15)_1041-1047 (2005).
Wang, et al., Curr. Can. Drug Targets 2(3):191-207 (2002).
Wang, et al., Mol. Can. Ther. 4(8):1214-1221 (2005).
Plymate, et al., Clin. Can. Res. 13(21):6429-6439 (2007).

* cited by examiner

IGF-IR ANTAGONISTS AS ADJUVANTS FOR TREATMENT OF PROSTATE CANCER

CROSS REFERENCE TO RELATED APPLICATIONS

This application claims priority to U.S. Application No. 60/765,072, filed Feb. 3, 2006, which is incorporated herein by reference in its entirety.

FEDERAL FUNDING

The present invention was made in part with United States Government support under Grant No. CA85859 from the National Institutes of Health, and Grant No. W81XWH-04-1-0912 from the Department of Defense. Accordingly, the United States Government has certain rights in this invention.

FIELD OF THE INVENTION

The present invention relates to a method of treating prostate cancer with androgen deprivation therapy and an insulin-like growth factor receptor (IGF-IR) antagonist. The method inhibits or delays transition of androgen dependent cancer to androgen independent cancer and significantly decreases risk of recurrence and improves treatment outcome.

BACKGROUND OF THE INVENTION

Prostate cancer is the most common nonskin cancer and second most common cause of cancer mortality in US men. Most prostate cancer is initially androgen dependent (AD). Prostate cancer cells initially require androgen for continued proliferation. Response to ablation of testosterone through androgen deprivation therapy (ADT), either surgically (orchiectomy) or medically (GnRH agonists or estrogens), leads to rapid induction of apoptosis of sensitive prostate cancer cells. The positive response rate is about 86% based on decrease in prostate specific antigen (PSA) and stabilization or decrease in tumor volume. The cell death that occurs generally takes place within the first few days to a week. However, the positive response is followed by a period of growth arrest in which remaining cells tend not to die. After 18-36 months following hormone ablation, growth recurs in 90% of cases. Invariably, surviving cancer cells become androgen independent or unresponsive, and androgen-independent (AI) tumor growth follows. Since ADT is initially very effective, a therapy that could take advantage of the benefits of ADT and extend or enhance its effects would be of great benefit.

Androgen independence appears to arise by a variety of mechanisms. Mutations in the androgen receptor gene are rare at diagnosis, but increase after exposure to the anti-androgen flutamide. However, these mutations do not occur in the majority of patients and do not explain most cases of hormone-refractory disease. High levels of bcl-2 are seen with greater frequency in advanced disease as compared to localized disease. Thus, the ability to induce apoptosis diminishes as the disease progresses. The proliferation of cells harboring mutations of the tumor suppressor gene p53, the loss of TGF-β receptors, and the expression of peptide growth factors likely play a role in the development of a hormone-refractory state. However, these processes do not explain the rapidity and frequency of development.

The insulin-like growth factor receptor (IGF-IR) is a ubiquitous transmembrane tyrosine kinase receptor that is essential for normal fetal and post-natal growth and development. IGF-IR can stimulate cell proliferation, cell differentiation, changes in cell size, and protect cells from apoptosis. It has also been considered to be quasi-obligatory for cell transformation (reviewed in Adams et al., *Cell. Mol. Life. Sci.* 57:1050-93 (2000); Baserga, *Oncogene* 19:5574-81 (2000)). IGF-IR is located on the cell surface of most cell types and serves as the signaling molecule for growth factors IGF-I and IGF-II (collectively termed henceforth IGFs). IGF-IR also binds insulin, albeit at three orders of magnitude lower affinity than it binds to IGFs. IGF-IR is a pre-formed hetero-tetramer containing two alpha and two beta chains covalently linked by disulfide bonds. The receptor subunits are synthesized as part of a single polypeptide chain of 180 kd, which is then proteolytically processed into alpha (130 kd) and beta (95 kd) subunits. The entire alpha chain is extracellular and contains the site for ligand binding. The beta chain possesses the transmembrane domain, the tyrosine kinase domain, and a C-terminal extension that is necessary for cell differentiation and transformation, but is dispensable for mitogen signaling and protection from apoptosis.

IGF-IR is highly similar to the insulin receptor (IR), particularly within the beta chain sequence (70% homology). Because of this homology, recent studies have demonstrated that these receptors can form hybrids containing one IR dimer and one IGF-IR dimer (Pandini et al., *Clin. Canc. Res.* 5:1935-19 (1999)). The formation of hybrids occurs in both normal and transformed cells and the hybrid content is dependent upon the concentration of the two homodimer receptors (IR and IGF-IR) within the cell. In one study of 39 breast cancer specimens, although both IR and IGF-IR were overexpressed in all tumor samples, hybrid receptor content consistently exceeded the levels of both homo-receptors by approximately 3-fold (Pandini et al., *Clin. Canc. Res.* 5:1935-44 (1999)). Although hybrid receptors are composed of IR and IGF-IR pairs, the hybrids bind selectively to IGFs, with affinity similar to that of IGF-IR, and only weakly bind insulin (Siddle and Soos, The IGF System. Humana Press. pp. 199-225. 1999). These hybrids therefore can bind IGFs and transduce signals in both normal and transformed cells.

Endocrine expression of IGF-I is regulated primarily by growth hormone and produced in the liver, but recent evidence suggests that many other tissue types are also capable of expressing IGF-I. This ligand is therefore subjected to endocrine and paracrine regulation, as well as autocrine in the case of many types of tumor cells (Yu, H. and Rohan, J., *J. Natl. Cancer Inst.* 92:1472-89 (2000)).

The androgen receptor (AR) consists of 3 functional and structural domains: an N-terminal (modulatory) domain; a DNA binding domain (Interpro Accession No. IPR001628) that mediates specific binding to target DNA sequences (ligand-responsive elements); and a hormone binding domain. The N-terminal domain (NTD) is unique to the androgen receptors and spans approximately the first 530 residues; the highly-conserved DNA-binding domain is smaller (around 65 residues) and occupies the central portion of the protein; and the hormone ligand binding domain (LBD) lies at the receptor C-terminus. In the absence of ligand, steroid hormone receptors are thought to be weakly associated with nuclear components; hormone binding greatly increases receptor affinity. The interaction among androgen receptor (AR), androgen, and prostate cancer is complex. Distribution of AR between the nucleus and cytoplasm is affected by androgen and androgen withdrawal. For example, AR immunoreactivity is observed only in the nuclei of LuCaP 35 cells grown in intact male mice, but strong immunoreactivity is observed in the cytoplasm and nuclei of LuCaP 35 grown in intact male mice and subsequently castrated.

SUMMARY OF THE INVENTION

This invention relates to treatment of androgen dependent tumors such as prostate cancer. Prostate tumors are typically stimulated by androgens such as testosterone, and exhibit androgen dependent (AD) growth. Therefore, treatment of prostate cancer typically involves therapy that deprives prostate cancer cells of androgen. However, a large proportion of prostate cancers eventually transition to androgen independence (AI). It has been discovered that administration of an IGF-IR antagonist in combination with androgen deprivation therapy (ADT) inhibits or prevents transition of AD tumors to AI tumors.

Accordingly, the invention provides a method of treatment of an androgen dependent cancer by administering androgen deprivation therapy and an IGF-IR antagonist. In an embodiment of the invention, the androgen dependent cancer is prostate cancer.

According to the invention, the IGF-IR antagonist can be an extracellular antagonist or an intracellular antagonist and more than one antagonist may be employed. More generally, the invention relates to inhibition of the IFG-IR signal transduction and to modulation of component of the pathway so as to inhibit transition of tumor cells from AD to AI. Extracellular antagonists include, but are not limited to proteins or other biological molecules that bind to IGF-IR or its ligand (IGF). In certain embodiments of the invention, the extracellular antagonist inhibits binding of IGF-IR to IGF. In one embodiment, the binding protein is an antibody, such as, for example, IMC-A12. In another embodiment, the binding protein is a soluble ligand binding fragment of IGF-IR. Intracellular IGF-IR antagonists can be biological molecules, but are usually small molecules. In an embodiment of the invention, the IGF-IR antagonist is a small molecule selected from AG1024, NVP-AEW541, and BMS-554417.

The effectiveness of various antagonists to inhibit IGF-IR signal transduction can be observed, for example, by assaying the state of IGF-IR signal transduction pathway components. In one embodiment, inhibition of IGF-IR is observed in the reduced phosphorylation of Akt. In another embodiment, inhibition of IGF-IR signaling is observed in the reduced expression of survivin or tubulin f-peptide (TUBB).

An IGF-IR antagonist of the invention is used with any form of ADT. In an embodiment of the invention, ADT comprises orchiectomy. In another embodiment of the invention, ADT comprises administration of a luteinizing hormone-releasing hormone analog. In another embodiment, ADT comprises administration of an antiandrogen. In yet another embodiment, an adrenal androgen inhibitor is administered. According to the invention, two or more methods of ADT can be combined.

The invention further provides for inhibition of signaling through Akt. Accordingly, the invention includes administration of modulators of signal transduction proteins that activate Akt. In one embodiment, such a modulator is an antagonist of EGFR.

According to the invention, an IGF-IR antagonist is administered as an adjuvant for ADT. In one embodiment, ADT and administration of an IGF-IR antagonist are initiated at about the same time. In another embodiment, ADT is initiated first, and an IGF-IR antagonist is administered before the androgen-independent cancer becomes androgen-independent. The invention further provides for use of anti-neoplastic agents with ADT and IGF-IR antagonist administration. In an embodiment of the invention, an IGF-IR antagonist and an ADT agent are used together as a neoadjuvant for surgical or radiation treatment of prostate cancer.

The invention also provides compositions comprising an IGF-IR antagonist and an ADT agent in a dosage form.

DETAILED DESCRIPTION OF THE INVENTION

Figure 1:
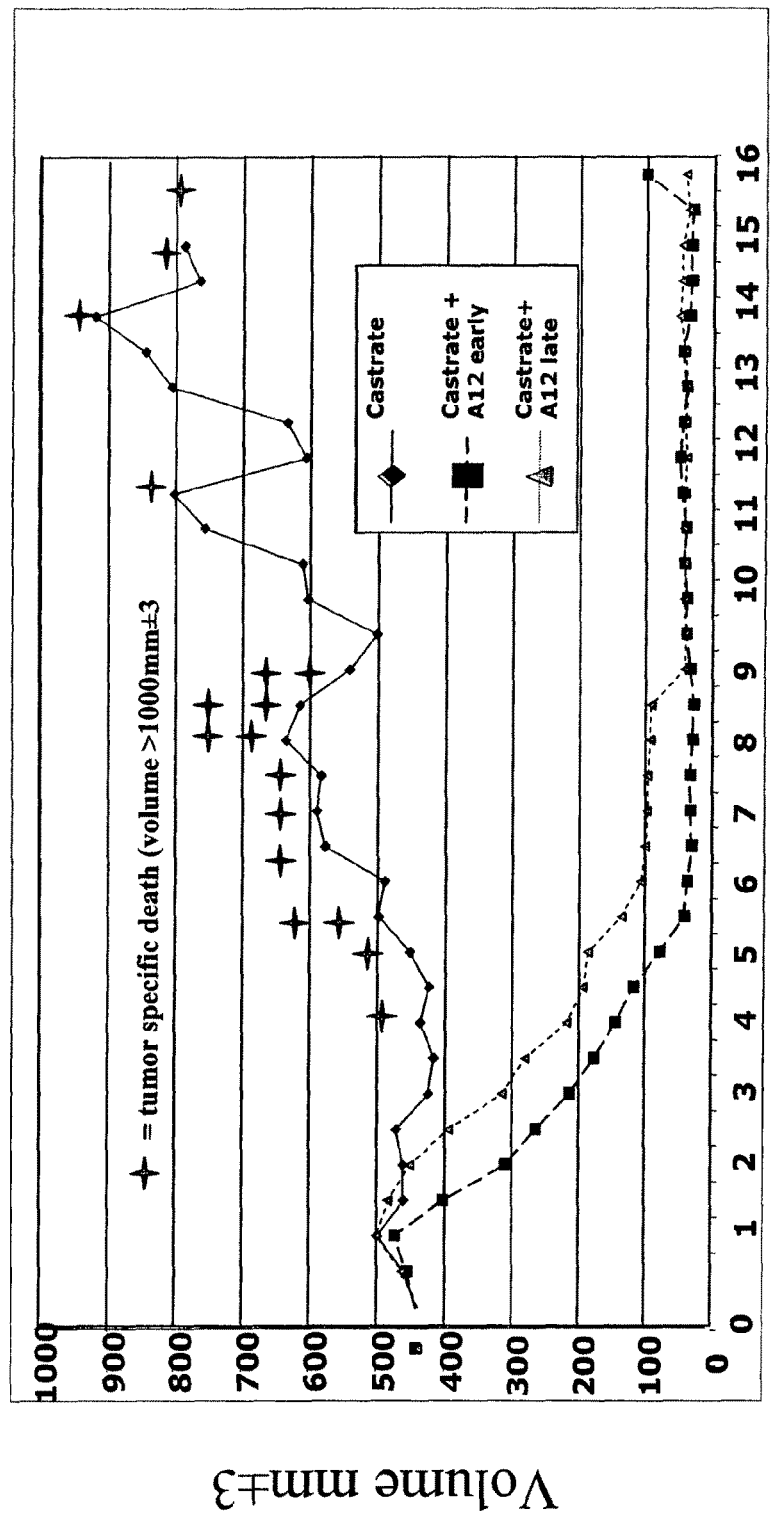
FIG. 1 depicts a study in which LuCap35 subcutaneous xenografts in SCID mice were observed. All mice were castrated when the average tumor size reached 400 mm$^3$. The control group of mice received castration alone. In two other groups, IMC-A12 was administered three times per week starting one or two weeks after castration.

It has been discovered that inhibitors of IGF-IR are useful in therapies for treatment of prostate cancer. In particular, administration of an IGF-IR antagonist in combination with androgen deprivation therapy (ADT) results in improved treatment outcome relative to ADT alone.

It has been observed that androgens up-regulate insulin-like growth factor-I receptor expression and may sensitize prostate cancer to the effects of IGF-I. Similarly, the transition to androgen independence that is observed in prostate cancer cells can result from adaptations of the cell that increase androgen receptor signaling such as increased levels of AR that make the cell sensitive to low levels of circulating androgen or AR mutations allowing activation by nonandrogen steroids. Indeed, evidence demonstrates that IGF-I signaling can actually mediate AR translocation to the nucleus of tumor cells and lead to up-regulation of AR-dependent genes. In this fashion, it is proposed that IGF-I can promote the conversion of androgen-dependent prostate cancer to androgen-independent, following hormone ablation therapy, by promoting AR signaling in the absence of circulating levels of androgen. Recent data from men and from human prostate xenografts has also shown that current methods of androgen ablation fail to decrease prostatic androgens to levels that no longer result in activation of the androgen receptor. The prostate may actually be able to synthesize DHT from several precursor steroids and possibly acetate.

It therefore follows that inhibition of IGF-I signaling concomitant with hormone ablation therapy may prevent or prolong the time until conversion of prostate cancer to androgen-independent disease, significantly delaying the onset of recurrence. Antagonists of IGF-IR may therefore be an effective adjuvant therapy to androgen deprivation strategies to treat newly diagnosed and locally advanced or metastatic hormone-dependent prostate cancer.

The use of IGF-IR antagonists with androgen withdrawal also has the potential to block IGF mediated recovery from apoptosis. Mechanisms by which IGF-IR can abrogate apoptosis include inhibition of ras-raf-map kinase, PI3 kinase including mTOR and forkhead signaling, and 14-3-3. Another mechanism by which IGF-IR inhibition can prolong the effects of androgen withdrawal is by maintaining the tumor in cell cycle arrest following initial apoptosis.

Previous studies have demonstrated that IGF-IR antagonists can have a positive effect when used to treat xenografts of both androgen dependent and androgen independent prostate cancers. Growth of the xenografts, while slowed, was not arrested or reversed. It has now been discovered that antagonists of IGF-IR are particularly useful for treatment of prostate cancer when administered with androgen deprivation therapy (ADT). Typically, prostate tumors transition to androgen independence, and become insensitive to ADT. As has been previously observed, such androgen insensitive tumors tend not to show strong responses to IGF-IR antagonists. However, as demonstrated herein, the time for progression of prostate tumors from AD to AI is significantly prolonged by a therapy that combines ADT with administration of an IGF-IR antagonist. During that extended period, the tumors diminish in size, and PSA levels are reduced. The combined therapy reduces the high risk of recurrence that is seen with ADT alone, and reduces the risk that metastatic cancer will develop. Treatment with an IGF-IR antagonists is also advantageous for treatment of advanced prostate cancer in which metastases potentially are present or have been diagnosed.

In models incorporating prostate cancer cells, AR translocation from cytoplasm to nucleus is observed to be induced not only by androgen stimulation, but also, though to a lesser extent, by IGF-IR stimulation. Even in the presence of androgen, AR translocation in the presence of androgen and IGF is reduced by an IGF-IR antagonist.

In the prostate, following castration, low levels of androgens are still detectable. It is also reported that expression of IGF-IR, which signals through Akt, first decreases in response to castration, but then increases, and further that growth factor stimulation of Akt enhances AR signaling to low levels of androgen.

As demonstrated herein, treatment with an IGF-IR antagonist significantly delays regrowth of tumors in castrated mice. Further, there is a good correlation between decreased nuclear AR and decreased tumor volume. This suggests that inhibition of IGF-IR signaling plays a considerable role in inhibiting AR driven tumor progression. In the experiments described herein, IGF-IR signaling is inhibited using an antibody designated A12, that binds to IGF-IR. Previous experiments with A12 and similar antibodies show that there is decreased phosphorylation (i.e., activation) of a various signal transduction molecules, including ERK and MAPK, and particularly Akt. The effect of inhibition of IGF-IR has been observed in a variety of tumor cell types, including the M12 prostate tumor line (Wu, J. D. et al., 2005, *Clin. Cancer Res.* 11:3065-74) and MCF7 breast cancer cells (Burtrum, D. et al., 2003, *Cancer Res.* 63:8912-21). Thus, it should be appreciated that the same or similar adjuvant activity observed herein for an IGF-IR antagonist would be observed for agents that exert the same or similar effect on Akt activation.

Treatment with an IGF-IR antagonist is observed to result in inhibition of AR translocation to the nucleus. The inhibition can be observed histochemically or by fluorescence microscopy, as well as in reduced expression levels of AR induced genes. Two genes associated with resistance to castration, survivin and tubulin β-peptide are regulated by IGF-IR through Akt activation. Expression of the genes is suppressed in castrated mice treated with an IGF-IR antagonist as compared to castration alone. Similar inhibitory effects on AR translocation and Akt activated gene expression would be observed in response to an Akt specific inhibitor or an antagonist of another signal transduction pathway involving Akt to a significant degree.

A variety of IGF-IR antagonists can be used according to the invention. The IGF-IR antagonists can be extracellular antagonists or intracellular antagonists. The extracellular and intracellular IGF-IR antagonists can be biological molecules, small molecules, or any other substance that inhibits activation of IGF-IR, for example by interaction with the extracellular binding region of the receptor (i.e., extracellular antagonist), by inhibiting phosphorylation of the intracellular tyrosine kinase domain of IGF-IR, or by inhibiting interaction with of activation of any other cellular component involved in the IGF-IR signaling pathway, thereby ultimately inhibiting gene activation or cellular proliferation.

In an embodiment of the present invention, an extracellular IGF-IR antagonist interacts with the extracellular ligand binding region of the receptor through sufficient physical or chemical interaction between the antagonist and the extracellular binding region of the receptor, such that binding of IGF-IR and its ligand (IGF) is blocked and tyrosine kinase activity of the receptor is inhibited. One of skill in the art would appreciate that examples of such chemical interactions, which include association or bonding, are known in the art and include covalent bonding, ionic bonding, hydrogen bonding, and the like between the antagonist and the extracellular binding region. In an embodiment of the invention, the extracellular IGF-IR antagonist is a biological molecule. Biological molecules include, but are not limited to, antibodies or antibody fragments that bind to IGF-IR. In another embodiment, the IGF-IR antagonist can be a small molecule that blocks ligand binding to IGF-IR. In another embodiment, the extracellular antagonist is a substance that sequesters or degrades IGF-IR ligands. One example is a soluble extracellular fragment of IGF-IR that binds to IGF. Another example of such a substance is an IGF binding protein (IGFBP) that can bind to IGF such as to limit IGF receptor activation, such as, for example, IGFBP-1, IGFBP-2, and IGFBP-3. In another embodiment of the invention, a small molecule inhibitor binds to the ligand binding domain of IGF-IR and blocks binding and receptor activation by an IGF-IR ligand.

Although not wishing to be bound by theory, it is thought that the extracellular IGF-IR antagonist inhibits all signal transduction cascades initiated by the conformation changes in the extracellular region of the IGF-IR following IGF-IR activation. This inhibition includes surface IGF-IR as well as those IGF-IR that have been internalized within a cell. For example, it is thought that activated receptor tyrosine kinases (RTKs) can be internalized via a clathrin-coated pit into an endosome, while still maintaining their signaling activity.

Following internalization, such receivers are either recycled back to the cell surface or degraded in the endosome or lysosome.

Another way to inhibit IGF-IR mediated signal transduction is by down-regulation IGF-IR expression. In an embodiment of the invention, an IGF-IR antagonist binds to the receptor and promotes receptor internalization and degradation. In another embodiment, an IGF-IR antagonist reduces expression of the receptor.

Biological molecules, in the context of the present invention, include all amino acids, nucleotides, lipids and polymers of monosaccharides that generally have a molecular weight greater than 650 D. Thus, biological molecules include, for example, oligopeptides, polypeptides, peptides, and proteins, oligonucleotides and polynucleotides such as, for example, DNA and RNA, and oligosaccharides and polysaccharides. Biological molecules further include derivatives of any of the molecules described above. For example, derivatives of biological molecules include lipids and glycosylation derivatives or oligopeptides, polypeptides, peptides, and proteins. Derivatives of biological molecules further include lipid derivatives of oligosaccharides and polysaccharides, e.g. lipopolysaccharides. Most typically, biological molecules are antibodies or functional derivatives thereof.

Small molecules include organic compounds, such as heterocycles, peptides, saccharides, steroids, and the like, organometallic compounds, salts of organic compounds and organometallic compounds, and inorganic compounds. Atoms in a small molecule are linked together via covalent and ionic bonds; the former is typical for small organic compounds such as small molecule tyrosine kinase inhibitors and the latter is typical of small inorganic compounds. The arrangement of atoms in a small organic molecule may represent a chain, e.g. a carbon-carbon chain or carbon-heteroatom chain or may represent a ring containing carbon atoms, e.g. benzene or a polycyclic system, or a combination of carbon and heteroatoms, i.e., heterocycles such as a pyrimidine or quinazoline. Although small molecules can have any molecular weight they generally include molecules that would otherwise be considered biological molecules, except their molecular weight is not greater than 650 D. Small molecules include both compounds found in nature, such as hormones, neurotransmitters, nucleotides, amino acids, sugars, lipids, and their derivatives as well as compounds made synthetically, either by traditional organic synthesis, bio-mediated synthesis, or a combination thereof. See e.g. Ganesan, *Drug Discov. Today* 7(1): 47-55 (January 2002); Lou, *Drug Discov. Today*, 6(24): 1288-1294 (December 2001). The compounds may be modified to enhance efficacy, stability, pharmaceutical compatibility, and the like.

The intracellular IGF-IR antagonists can be biological molecules, such as mutant receptor subunits, intracellular binding proteins (e.g., intracellularly expressed fragments of antibodies) and the like. In a preferred embodiment, the intracellular antagonists are small molecules. The small molecule inhibitors include but are not limited to small molecules that modify or block the ATP binding domain, substrate binding regions, or kinase domain of IGF-IR. The small molecule inhibitors also include substances that are inhibitors of other components of the IGF-IR signal transduction pathway, including, but not limited to, ras-mitogen activated protein kinase (MAPK) pathway, and the phospatidylinositol-3 kinase (PI3K)-Akt pathway.

To identify antagonists, small molecule libraries can be screened for inhibitory activity using high-throughput biochemical, enzymatic, or cell based assays. The assays can be formulated to detect the ability of a test compound to inhibit binding of IGF-IR to IGF-IR ligands or substrate IRS-1 or to inhibit the formation of functional receptors from IGF-IR dimers. The intracellular IGF-IR antagonist may inhibit the tyrosine kinase activity of IGF-IR by binding to or inhibiting activation of the intracellular region bearing a kinase domain or by binding to or inhibiting activation of any intracellular protein involved in the signaling pathway of IGF-IR. Small molecule antagonists of IGF-IR include, for example, the insulin-like growth factor-I receptor selective kinase inhibitors NVP-AEW541 (García-Echeverria, C. et al., 2004, *Cancer Cell* 5:231-9) and NVP-ADW742 (Mitsiades, C. et al., 2004, *Cancer Cell* 5:221-30), INSM-18 (Insmed Incorporated), which selectively inhibits IGF-IR and HER2, and the tyrosine kinase inhibitor tryphostins AG1024 and AG1034 (Párrizas, M. et al., 1997, *Endocrinology* 138:1427-33) which inhibit phosphorylation by blocking substrate binding and have a significantly lower $IC_{50}$ for inhibition of IFG-IR phosphorylation than for IR phosphorylation. The cyclolignan derivative picropodophyllin (PPP) is another IGF-IR antagonist that inhibits IGF-IR phosphorylation without interfering with IR activity (Gimita, A. et al., 2004, *Cancer Res.* 64:236-42). Other small molecule IGF-IR antagonists include the benzimidazol derivatives BMS-536924 (Wittman, M. et al., 2005, *J. Med. Chem.* 48:5639-43) and BMS-554417 (Haluska P. et al., 2006, *CancerRes.* 66:362-71), which inhibit IGF-IR and IR almost equipotently. For compounds that inhibit receptors in addition to IGF-IR, it should be noted that $IC_{50}$ values measured in vitro in direct binding assays may not reflect $IC_{50}$ values measured-ex vivo or in vivo (i.e., in intact cells or organisms). For example, where it is desired to avoid inhibition of IR, a compound that inhibits IR in vitro may not significantly affect the activity of the receptor when used in vivo at a concentration that effectively inhibits IGF-IR.

Antisense oligodeoxynucleotides, antisense RNAs and small inhibitory RNAs (siRNA) provide for targeted degradation of mRNA, thus preventing the translation of proteins. Accordingly, expression of receptor tyrosine kinases and other proteins critical for IGF signaling can be inhibited. The ability of antisense oligonucleotides to suppress gene expression was discovered more than 25 yr ago (Zamecnik and Stephenson, 1978, *Proc. Natl. Acad. Sci. USA.* 75:280-84). Antisense oligonucleotides base pair with mRNA and pre-mRNAs and can potentially interfere with several steps of RNA processing and message translation, including splicing, polyadenylation, export, stability, and protein translation (Sazani and Kole, 2003, *J. Clin. Invest.* 112:481-86). However, the two most powerful and widely used antisense strategies are the degradation of mRNA or pre-mRNA via RNaseH and the alteration of splicing via targeting aberrant splice junctions. RNaseH recognizes DNA/RNA heteroduplexes and cleaves the RNA approximately midway between the 5' and 3' ends of the DNA oligonucleotide. Inhibition of IGF-IR by antisense oligonucleotides is exemplified in Wraight, *Nat. Biotechnol.* 18:521-6.

Innate RNA-mediated mechanisms can regulate mRNA stability, message translation, and chromatin organization (Mello and Conte, 2004, *Nature.* 431:338-42). Furthermore, exogenously introduced long double-stranded RNA (dsRNA) is an effective tool for gene silencing in a variety of lower organisms. However, in mammals, long dsRNAs elicit highly toxic responses that are related to the effects of viral infection and interferon production (Williams, 1997, *Biochem. Soc. Trans.* 25:509-13). To avoid this, Elbashir and colleagues (Elbashir, et al., 2001, *Nature.* 411:494-98) initiated the use of siRNAs composed of 19-mer duplexes with 5' phosphates and 2 base 3' overhangs on each strand, which selectively degrade targeted mRNAs upon introduction into cells.

The action of interfering dsRNA in mammals usually involves two enzymatic steps. First, Dicer, an RNase III-type enzyme, cleaves dsRNA to 21-23-mer siRNA segments. Then, RNA-induced silencing complex (RISC) unwinds the RNA duplex, pairs one strand with a complementary region in a cognate mRNA, and initiates cleavage at a site 10 nucleotides upstream of the 5' end of the siRNA strand (Hannon, 2002, *Nature.* 418:244-51). Short, chemically synthesized siRNAs in the 19-22 mer range do not require the Dicer step and can enter the RISC machinery directly. It should be noted that either strand of an RNA duplex can potentially be loaded onto the RISC complex, but the composition of the oligonucleotide can affect the choice of strands. Thus, to attain selective degradation of a particular mRNA target, the duplex should favor loading of the antisense strand component by having relatively weak base pairing at its 5' end (Khvorova, 2003, *Cell* 115:209-16). Exogenous siRNAs can be provided as synthesized oligonucleotides or expressed from plasmid or viral vectors (Paddison and Hannon, 2003, *Curr. Opin. Mol. Ther.* 5:217-24). In the latter case, precursor molecules are usually expressed as short hairpin RNAs (shRNAs) containing loops of 4-8 nucleotides and stems of 19-30 nucleotides; these are then cleaved by Dicer to form functional siRNAs.

Anti-IGF-IR antibodies to be used according to the present invention exhibit one or more of following properties:

1) The antibodies bind to the external domain of IGF-IR and inhibit binding of IGF-I or IGF-II to IGF-IR. Inhibition can be determined, for example, by a direct binding assay using purified or membrane bound receptor. In this embodiment, the antibodies of the present invention, or fragments thereof, preferably bind IGF-IR at least as strongly as the natural ligands of IGF-IR (IGF-I and IGF-II).

2) The antibodies neutralize IGF-IR. Binding of a ligand, e.g., IGF-I or IGF-II, to an external, extracellular domain of IGF-IR stimulates autophosphorylation of the beta subunit and phosphorylation of IFG-IR substrates, including MAPK, Akt, and IRS-1.

Neutralization of IGF-IR includes inhibition, diminution, inactivation and/or disruption of one or more of these activities normally associated with signal transduction. Neutralization can be determined in vivo, ex vivo, or in vitro using, for example, tissues, cultured cell, or purified cellular components. Neutralization includes inhibition of IGF-IR/IR heterodimers as well as IGF-IR homodimers. Thus, neutralizing IGF-IR has various effects, including inhibition, diminution, inactivation and/or disruption of growth (proliferation and differentiation), angiogenesis (blood vessel recruitment, invasion, and metastasis), and cell motility and metastasis (cell adhesion and invasiveness).

One measure of IGF-IR neutralization is inhibition of the tyrosine kinase activity of the receptor. Tyrosine kinase inhibition can be determined using well-known methods; for example, by measuring the autophosphorylation level of recombinant kinase receptor, and/or phosphorylation of natural or synthetic substrates. Thus, phosphorylation assays are useful in determining neutralizing antibodies in the context of the present invention. Phosphorylation can be detected, for example, using an antibody specific for phosphotyrosine in an ELISA assay or on a western blot. Some assays for tyrosine kinase activity are described in Panek et al., 1997, *J. Pharmacol. Exp. Thera.* 283: 1433-44 and Batley et al., 1998, *Life Sci.* 62:143-50. Antibodies of the invention cause a decrease in tyrosine phosphorylation of IGF-IR of at least about 75%, preferably at least about 85%, and more preferably at least about 90% in cells that respond to ligand.

Another measure of IGF-IR neutralization is inhibition of phosphorylation of downstream substrates of IGF-IR. Accordingly, the level of phosphorylation of MAPK, Akt, or IRS-1 can be measured. The decrease in substrate phosphorylation is at least about 50%, preferably at least about 65%, more preferably at least about 80%.

In addition, methods for detection of protein expression can be utilized to determine IGF-IR neutralization, wherein the proteins being measured are regulated by IGF-IR tyrosine kinase activity. An example of such a protein that is associated with cancer progression and drug resistance is survivin, which is a member of the inhibitor of apoptosis (IAP) family. While survivin regulation is complex and mediated by more than one pathway, regulation mediated by Akt and increased by IGF-1 has been demonstrated. See, e.g., Zhang et al., 2005, *Oncogene,* 24:2474-82. Methods for analyzing gene expression include immunohistochemistry (IHC) for detection of protein expression, fluorescence in situ hybridization (FISH) for detection of gene amplification, competitive radioligand binding assays, solid matrix blotting techniques, such as Northern and Southern blots, reverse transcriptase polymerase chain reaction (RT-PCR) and ELISA. See, e.g., Grandis et al., 1996, *Cancer,* 78:1284-92; Shimizu et al., 1994, *Japan J. Cancer Res.,* 85:567-71; Sauter et al., 1996, *Am. J. Path.,* 148:1047-53; Collins, 1995, *Glia* 15:289-96; Radinsky et al., 1995, *Clin. Cancer Res.* 1:19-31; Petrides et al., 1990, *Cancer Res.* 50:3934-39; Hoffmann et al., 1997, *Anticancer Res.* 17:4419-26; Wikstrand et al., 1995, *Cancer Res.* 55:3140-48.

Ex vivo assays can also be utilized to determine IGF-IR neutralization. For example, receptor tyrosine kinase inhibition can be observed by mitogenic assays using cell lines stimulated with receptor ligand in the presence and absence of inhibitor. The MCF7 breast cancer line (American Type Culture Collection (ATCC), Rockville, Md.) is such a cell line that expresses IGF-IR and is stimulated by IGF-I or IGF-II. Another method involves testing for inhibition of growth of IGF-IR-expressing tumor cells or cells transfected to express IGF-IR. Inhibition can also be observed using tumor models, for example, human tumor cells injected into a mouse.

The antibodies of the present invention are not limited by any particular mechanism of IGF-IR neutralization. The anti-IGF-IR antibodies of the present invention can bind externally to the IGF-1 cell surface receptor, block binding of ligand (e.g., IGF-I or IGF-II) and subsequent signal transduction mediated via the receptor-associated tyrosine kinase, and prevent phosphorylation of the IGF-IR and other downstream proteins in the signal transduction cascade.

3) The antibodies down modulate IGF-IR. The amount of IGF-IR present on the surface of a cell depends on receptor protein production, internalization, and degradation. The amount of IGF-IR present on the surface of a cell can be measured indirectly, by detecting internalization of the receptor or a molecule bound to the receptor. For example, receptor internalization can be measured by contacting cells that express IGF-IR with a labeled antibody. Membrane-bound antibody is then stripped, collected and counted. Internalized antibody is determined by lysing the cells and detecting label in the lysates.

Another way is to directly measure the amount of the receptor present on the cell following treatment with an anti-IGF-IR antibody or other substance, for example, by fluorescence-activated cell-sorting analysis of cells stained for surface expression of IGF-IR. Stained cells are incubated at 37° C. and fluorescence intensity measured over time. As a control, part of the stained population can be incubated at 4° C. (conditions under which receptor internalization is halted).

Cell surface IGF-IR can be detected and measured using a different antibody that is specific for IGF-IR and that does not block or compete with binding of the antibody being tested. (Burtrum, et al., 2003, *Cancer Res.* 63:8912-21) Treatment of an IGF-IR expressing cell with an antibody of the invention results in reduction of cell surface IGF-IR. In a preferred embodiment, the reduction is at least about 70%, more preferably at least about 80%, and even more preferably at least about 90% in response to treatment with an antibody of the invention. A significant decrease can be observed in as little as four hours.

Another measure of down-modulation is reduction of the total receptor protein present in a cell, and reflects degradation of internal receptors. Accordingly, treatment of cells (particularly cancer cells) with antibodies of the invention results in a reduction in total cellular IGF-IR. In a preferred embodiment, the reduction is at least about 70%, more preferably at least about 80%, and even more preferably at least about 90%.

For treatment of human subjects, the antibodies are preferably human antibodies, but can also be humanized or chimeric antibodies. One preferred human antibody that binds to IGF-IR is A12 (See, WO2005016970). Another preferred human antibody is 2F8 (See, WO2005016970). Useful antibodies further include anti-IGF-IR antibodies that compete with IMC-A12 or IMC-2F8 for binding to IGF-IR, as well as antibodies that bind to other epitopes. (i.e., antibodies that bind to other epitopes and exhibit properties as previously described such as ligand blocking, receptor internalization, etc., but do not compete with IMC-A12 or IMC-2F8). Other nonlimiting examples of neutralizing anti-IGF-IR antibodies useful according to the invention are described by Wang et al. (WO 2003/1000008; US 2004/0018191) and Singh et al. (WO 2003/106621; US 2003/0235582). The nucleotide and amino acid sequences of several antibodies mentioned herein are indexed in Table 1.

TABLE 1

SEQ ID NOS for Antibody Variable Domains and CDRs (nucleotide/amino acid)

| Antibody Name | VH | CDRH1 | CDRH2 | CDRH3 | VL | CDRL1 | CDRL2 | CDRL3 |
|---|---|---|---|---|---|---|---|---|
| A12 | 1/2 | 13/14 | 15/16 | 17/18 | 9/10 | 25/26 | 27/28 | 29/30 |
| 2F8 | 1/2 | 13/14 | 15/16 | 17/18 | 5/6 | 19/20 | 21/22 | 23/24 |
| 11F8 | 37/38 | 31/32 | 33/34 | 35/36 | 45/46 | 39/40 | 41/42 | 43/44 |
| C225 | 47/48 | | | | 49/50 | | | |

Antibodies that can be used according to the invention include complete immunoglobulins, antigen binding fragments of immunoglobulins, as well as antigen binding proteins that comprise antigen binding domains of immunoglobulins. Antigen binding fragments of immunoglobulins include, for example, Fab, Fab', and F(ab')$_2$. Other antibody formats have been developed which retain binding specificity, but have other characteristics that may be desirable, including for example, bispecificity, multivalence (more than two binding sites), compact size (e.g., binding domains alone).

Single chain antibodies comprise two variable domains lack some or all of the constant domains of the whole antibodies from which they are derived. Therefore, they can overcome some of the problems associated with the use of whole antibodies. For example, single-chain antibodies tend to be free of certain undesired interactions between heavy-chain constant regions and other biological molecules. Additionally, single-chain antibodies are considerably smaller than whole antibodies and can have greater permeability than whole antibodies, allowing single-chain antibodies to localize and bind to target antigen-binding sites more efficiently. Furthermore, the relatively small size of single-chain antibodies makes them less likely to provoke an unwanted immune response in a recipient than whole antibodies.

Multiple single chain antibodies, each single chain having one $V_H$ and one $V_L$ domain covalently linked by a first peptide linker, can be covalently linked by at least one or more peptide linker to form a multivalent single chain antibodies, which can be monospecific or multispecific. Each chain of a multivalent single chain antibody includes a variable light chain fragment and a variable heavy chain fragment, and is linked by a peptide linker to at least one other chain. The peptide linker is composed of at least fifteen amino acid residues. The maximum number of amino acid residues is about one hundred.

Two single chain antibodies can be combined to form a diabody, also known as a bivalent dimer. Diabodies have two chains and two binding sites, and can be monospecific or bispecific. Each chain of the diabody includes a $V_H$ domain connected to a $V_L$ domain. The domains are connected with linkers that are short enough to prevent pairing between domains on the same chain, thus driving the pairing between complementary domains on different chains to recreate the two antigen-binding sites. Similarly, three single chain antibodies can be combined to form a triabody, also known as a trivalent trimer. Triabodies are constructed with the amino acid terminus of a $V_L$ or $V_H$ domain directly fused to the carboxyl terminus of a $V_L$ or $V_H$ domain (i.e., without any linker sequence). Triabodies can be monospecific, bispecific or trispecific. Bispecific antibodies that are bivalent for each antigen binding site have also been developed. For example, Zhu (WO 01/90192) describes an antibody with four binding sites that otherwise has the structure of, and retains the effector functions of, a naturally occurring antibody. Zhu (WO 2006/020258) discloses a bispecific antibody that incorporates two diabodies and Ig constant regions.

Thus, antibodies of the invention and fragments thereof include, but are not limited to, naturally occurring antibodies, bivalent fragments such as (Fab')$_2$, monovalent fragments such as Fab, single chain antibodies, single chain Fv (scFv), single domain antibodies, multivalent single chain antibodies, diabodies, triabodies, and the like that bind specifically with antigens.

IGF-IR antogonists are exemplified herein by IMC-A12, a human monoclonal antibody that binds to the extracellular domain of IGF and blocks binding of IGF. Properties of IMC-A 12 and a similar human antibody are provided in International Publication WO 2005/016970.

Effects of IGF-IR antagonists of the invention on androgen dependent prostate cancer cells include one or more of the following. 1) IGF can mediate AR activation or translocation in the absence of androgen. IGF-IR antagonists of the invention block IGF mediated translocation. 2) IGF-IR antagonists mediate enhance cell killing or inhibition of tumor cell proliferation. 3) AR mediated androgen receptor activated gene expression is reduced. Genes demonstrating AR mediated expression include, for example, PSA and TMPRSS2 (a transmembrane serine protease).

According to the invention, an IGF-IR antagonist is administered to a subject having prostate cancer in coincidence with androgen deprivation therapy (ADT; also call hormonal therapy). The goal of ADT is to lower levels of the male hormones (androgens, such as testosterone) in the body. Androgens, produced mainly in the testicles, can actually stimulate prostate cancer cells to grow. Lowering androgen levels can usually make prostate cancers shrink or grow more slowly.

ADT is used in several situations: as first-line (initial) therapy for patients unable to have surgery or radiation or that can't be cured by these treatments because the cancer has already spread beyond the prostate gland; after initial treatment, such as surgery or radiation therapy, if the cancer remains or comes back; as an addition (adjuvant) to radiation therapy as initial treatment in certain groups of men at high risk for cancer recurrence; and before surgery or radiation (neoadjuvant therapy), in an attempt to shrink the cancer and make the other treatment more effective. According to the invention, an IGF-IR antagonist is administered in conjunction with ADT in any situation where ADT would otherwise be employed. The IGF-IR antagonist is an adjuvant that enhances and/or prolongs the effect of ADT.

There are several methods used for ADT. Orchiectomy involves removal of the testicles, where more than 90% of the androgens, mostly testosterone, are produced. With this source removed, most prostate cancers shrink. Although permanent and resulting in a variety of undesirable side effects generally related to changing levels of hormones in the body, orchiectomy is probably the least expensive and simplest way to reduce androgen production and can be done as a simple outpatient procedure.

Luteinizing hormone-releasing hormone (LHRH) analogs (also called LHRH agonists) lower testosterone levels as effectively as orchiectomy by decreasing the androgens, mainly testosterone, produced by the testicles. LHRH analogs are injected or placed as small implants under the skin and are given either monthly or every 3, 4, 6, or 12 months. Examples of LHRH analogs include leuprolide, goserelin, and triptorelin. Possible side effects of LHRH analogs are similar to those of orchiectomy, and are largely due to changes in hormone levels.

Antiandrogens block the body's ability to use any androgens. Even after orchiectomy or during treatment with LHRH analogs, a small amount of androgens is still produced by the adrenal glands. Drugs of this type include flutamide, bicalutamide, and nilutamide. These drugs are usually taken daily as pills.

Antiandrogen treatment is often combined with orchiectomy or LHRH analogs. This combination is called combined androgen blockade (CAB). Further, an antiandrogen may be added if treatment with orchiectomy or an LHRH analog is no longer working by itself. Several recent studies have compared the effectiveness of antiandrogens alone with that of LHRH agonists. Most found no difference in survival rates, but a few found antiandrogens to be slightly less effective.

Side effects of antiandrogens in patients already treated by orchiectomy or with LHRH agonists are usually not serious. Diarrhea is the major side effect, although nausea, liver problems, and tiredness can also occur. The major difference from LHRH agonists is that antiandrogens have fewer sexual side effects and allow maintenance of libido and potency if used alone.

Adrenal androgen inhibitors can be administered because the low level of androgens produced by the adrenal glands may be sufficient to provide continued stimulation. Following androgen ablation, a subset of prostate cancer cells can become hypersensitive to androgens and the adrenal gland is the source of 5 to 10% of peripheral testosterone. The two most commonly used agents to inhibit adrenal androgen production are aminoglutethimide and ketoconazole.

Other examples of androgen-suppressing drugs include diethylstilbestrol (DES), megesterol acetate, cyproterone acetate, and prednisone Estrogens were once the main alternative to orchiectomy for men with advanced prostate cancer, but because of their possible side effects, which include blood clots and breast enlargement, estrogens have been largely replaced by LHRH analogs and antiandrogens.

According to the invention, a course of treatment with an IGF-IR antagonist is administered starting before, at the time of, or after initiation of ADT. The course of administration of an IGF-IR antagonist should coincide with ADT, but the coincidence need not be complete. For example, the IGF-IR antagonist can be administered any time during remission resulting from androgen withdrawal. In an embodiment of the invention, the IGF-IR antagonist is administered within 24 months of androgen withdrawal for treatment of a primary or metastatic tumors. In another embodiment, the IGF-IR antagonist is administered within 18 months of androgen withdrawal. In an embodiment of the invention, the IGF-IR antagonist is administered during or near the end of the cell death period observed upon ADI treatment, and will still prevent or delay the subsequent outgrowth of AI cells. In an embodiment of the invention, administration of the IGF-IR antagonist is initiated within two weeks of androgen withdrawal. In another embodiment, administration is begun within one week of androgen withdrawal.

IGF-IR antagonists of the invention can be administered with antagonists that neutralize other receptors involved in tumor growth. Of particular interest are receptors involved in a signal transduction pathway includes Akt. For example, signal transduction through EGFR or HER2 (erbB2) is thought to involve Akt activation. Accordingly, IGF-IR antagonists of the invention may be combined with intracellular or extracellular antagonists of EGFR or HER2.

Antagonists of EGFR or HER2 include antigen-binding proteins that bind to the extracellular domain of EGFR or HER2 and block binding of one or more ligands and/or neutralize ligand-induced activation. The antagonists also include antibodies or other binding proteins that bind to a ligand of EGFR and inhibits binding of EGFR to the ligand. Ligands for EGFR include, for example, EGF, TGF-α, amphiregulin, heparin-binding EGF (HB-EGF) and betacellulin. EGF and TGF-α are thought to be the main endogenous ligands that result in EGFR-mediated stimulation, although TGF-α has been shown to be more potent in promoting angiogenesis. EGFR antagonists also include substances that inhibit EGFR dimerization with other EGFR receptor subunits (i.e., EGFR homodimers) or heterodimerization with other growth factor receptors (e.g., HER2). EGFR antagonists further include biological molecules and small molecules, such as synthetic kinase inhibitors that act directly on the cytoplasmic domain of EGFR to inhibit EGFR-mediated signal transduction. Erbitux® (cetuximab; C225) is an example of an EGFR antagonist antibody that binds to EGFR and blocks ligand binding. Erbitux® is a chimeric IgG1 antibody having murine variable domains of M225 (See, e.g., WO 96/40210) and human constant domains. A human anti-EGFR antibody designated 11F8 is disclosed by Zhu (WO 2005/090407). Other anti-EGFR antibodies include EMD 72000 (matuzumab), Vectibix™ (panitumumab; ABX-EGF), TheraCIM (nimotuzumab), and Hu-Max-EGFR (zalutumumab). An example of a small molecule EGFR antagonist is IRESSA™ (ZD1939), which is a quinozaline derivative that functions as an ATP-mimetic to inhibit EGFR. See U.S. Pat. No. 5,616,582 (Zeneca Limited). Another example of a small molecule EGFR antagonist is TARCEVA™ (OSI-774), which is a 4-(substitutedphenylamino)quinozaline derivative [6,7-Bis(2-methoxy-ethoxy)-quinazolin-4-yl]-(3-ethynyl-phenyl)amine hydrochloride] EGFR inhibitor. See WO 96/30347 (Pfizer Inc.); Moyer et al., *Cancer Res.*, 57: 4838-48 (1997); Pollack et al., *J. Pharmacol.*, 291: 739-48 (1999). TARCEVA™ may function by inhibiting phosphorylation of EGFR and its downstream PI3/Akt and MAP (mitogen activated protein) kinase signal transduction pathways resulting in p27-mediated cell-cycle arrest. See Hidalgo et al., Abstract 281 presented at the 37th Annual Meeting of ASCO, San Francisco, Calif., 12-15 May 2001.

While the antagonists can be administered separately, in certain instances, it can be desirable to combine the functions of two antagonists into a single molecule, such as a bispecific antibody or a dual inhibitor. Bispecific antibodies can be engineered to combine IGF-IR specificity with specificity for a different RTK or other cell surface molecule. Combinations of IGF-IR specificity with EGFR specificity of HER2 specificity are of particular interest. An example of a bispecific antibody that binds to IGF-IR and EGFR is provided by Zhu (WO 2006/020258). Similarly, small molecules that inhibit IGF-IR and a second cellular component are available, or can be screened for. For example as mentioned above, INSM-18 (Insmed/University of California San Franscisco) inhibits IGF-IR and HER2/neu.

Another aspect of the present invention relates to pharmaceutical compositions containing the antagonists of the present invention or a pharmaceutically acceptable salt, hydrate or pro-drug thereof, in combination with a pharmaceutically acceptable carrier. Such compositions may be separate compositions of the IGF-IR antagonist and the ADT agent or a single composition containing both.

The compositions of the present invention may be in solid or liquid form, in solution or in suspension. Routes of administration include, for example, oral, parenteral (intravenous, intraperitoneal, subcutaneous, or intramuscular), topical, transdermal and by inhalation.

For oral administration, the IGF-IR antagonist may be administered, for example, in liquid form with an inert diluent or assimilable carrier, or incorporated into a solid dosage form. Examples of oral liquid and solid dosage forms include, for example, solutions, suspensions, syrups, emulsions, tablets, lozenges, capsules (including soft gelatin capsules), and the like. Oral dosage forms may be formulated as sustained release products using, for example, a coating to delay disintegration or to control diffusion of the active compound. Where necessary, the compositions may also include a solubilizing agent.

Examples of injectable dosage forms include sterile injectable liquids, including, for example, solutions, emulsions and suspensions. Injectable dosage forms further include solids such as sterile powders that are reconstituted, dissolved or suspended in a liquid prior to injection. Sterile injectable solutions are prepared by incorporating the EGF-IR antagonist and/or the ADT agent in the required amount in the appropriate solvent with various of the other ingredients enumerated above, as required, followed by filtered sterilization.

Carriers typically include, for example, sterile water, saline, injectable organic esters, peanut oil, vegetable oil, and the like. Buffering agents, preservatives, and the like can be included in the administrable forms. Sterile formulations can be prepared by heating, irradiation, microfiltration, and/or by addition of various antibacterial and antifungal agents, such as, for example, parabens, chlorobutanol, phenol, sorbic acid, thimerosal, and the like.

For topical administration, IGF-IR antagonists and the ADT agents of the present invention can be administered separately or together, for example, in the form of gels, creams, or ointments, or paints. Typical carriers for such application include hydrophobic or hydrophilic bases, oleaginous or alcoholic liquids, and dry powders. IGF-IR antagonists and ADT agents may also be incorporated in a gel or matrix base for application in a patch, optionally providing for controlled release of compound through a transdermal barrier. IGF-IR antagonists and ADT agents can also be formulated by known methods for rectal administration.

For administration by inhalation, IGF-IR antagonists and ADT agents of the present invention may be dissolved or suspended in, or adsorbed onto, a suitable carrier for use in a nebulizer, aerosol, or dry powder inhaler.

Suitable dosages can be determined by a physician or qualified medical professional, and depend on factors such as the nature of the illness being treated, the route of administration, the duration of treatment, and the condition of the patient. The IGF-IR antagonists and ADT agents may be administered as frequently as necessary in order to obtain the desired therapeutic effect. Frequency of administration will depend, for example, on the nature of the dosage form used. One of skill in the art would understand that dosages and frequency of treatment depend on the tolerance of the individual patient and on the pharmacological and pharmacokinetic properties of blocking or inhibitory agent used Ideally, one wishes to achieve saturable pharmacokinetics for the agent used. A loading dose for an anti-IGF-IR antibody can range, for example, from about 10 to about 1000 $mg/m^2$, preferably from about 200 to about 400 $mg/m^2$. This can be followed by several additional daily or weekly dosages ranging, for example, from about 200 to about 400 $mg/m^2$. An exemplary dosage of an IGF-IR antibody is 400 $mg/m^2$ loading and 250 $mg/m^2$ weekly infusion. (For conversions between mg/kg and $mg/m^2$ for humans and other mammals, see Freireich, E. J. et al., 1966, Cancer Chemother. Rep. 50:219-44.) The patient is monitored for side effects and the treatment is stopped when such side effects are severe. Effective dosages of the ADT agents are well known in the art.

One of skill in the art would also know how to monitor the progress of the treatment in order to determine an effective dose. For prostate cancer, one such way is to monitor PSA levels. Another is to monitor prostatic acid phosphatase (PAP). Other ways to monitor prostate cancers include ultrasound, computed tomography (CT), magnetic resonance imaging (MRI), and the like. Tissue samples can also be examined for expression and cellular distribution of AR, as well as expression of survivin and/or TUBB.

In certain embodiments of the invention, treatments combining administration of IGF-IR antagonists with ADT can employ with one or more anti-neoplastic agents. For example, as noted above, ADT is often employed as a neoadjuvant for radiation treatment of prostate tumors. When the anti-neoplastic agent is radiation, the source of the radiation can be either external (external beam radiation therapy—EBRT) or internal (brachytherapy—BT) to the patient being treated.

The anti-neoplastic agent can be an alkylating agent or an anti-metabolite. Examples of alkylating agents include, but are not limited to, cisplatin, cyclophosphamide, melphalan, and dacarbazine. Examples of anti-metabolites include, but not limited to, doxorubicin, daunorubicin, and paclitaxel, gemcitabine.

Useful anti-neoplastic agents also include mitotic inhibitors, such as taxanes docetaxel and paclitaxil. Topoisomerase inhibitors are another class of anti-neoplastic agents that can be used in combination with antibodies of the invention. These include inhibitors of topoisomerase I or topoisomerase II. Topoisomerase I inhibitors include irinotecan (CPT-11), aminocamptothecin, camptothecin, DX-8951f, topotecan. Topoisomerase II inhibitors include etoposide (VP-16), and teniposide (VM-26). Other substances are currently being evaluated with respect to topoisomerase inhibitory activity and effectiveness as anti-neoplastic agents. In a preferred embodiment, the topoisomerase inhibitor is irinotecan (CPT-11).

Throughout this application, various publications, reference texts, textbooks, technical manuals, patents, and patent applications are referred to. The teachings and disclosures of these publications, patents, patent applications and other documents in their entireties are hereby incorporated by reference into this application to more fully describe the state of the art to which the present invention pertains.

It is to be understood and expected that variations in the principles of invention herein disclosed may be made by one skilled in the art and it is intended that such modifications are to be included within the scope of the present invention.

The following examples further illustrate the invention, but should not be construed to limit the scope of the invention in any way. Detailed descriptions of conventional methods, such as those employed in the construction of vectors and plasmids, and expression of antibodies and antibody fragments can be obtained from numerous publications, including Sambrook, J et al., (1989) Molecular Cloning: A Laboratory Manual, $2^{nd}$ ed., Cold Spring Harbor Laboratory Press; Coligan, J. et al. (1994) Current Protocols in Immunology, Wiley & Sons, Incorporated; Enna, S. J. et al. (1991) Current Protocols in Pharmacology, Wiley & Sons, Bonifacino, J. S. et al. (1999) Current Protocols in Cell Biology, Wiley & Sons. All references mentioned herein are incorporated in their entirety.

EXAMPLES

Antagonism of IGF-IR Inhibits Tumor Regrowth Following ADT

A preclinical model was developed to test the efficacy of inhibition of IGF-IR signaling using a human monoclonal IGF-IR antibody (IMC-A12) with castration on recurrence of prostate cancer following castration. For the study, a xenograft of LuCaP 35, an androgen responsive human prostate cancer cell line, was implanted subcutaneously into the flank of male SCID mice. LuCaP 35 can transition to an androgen-independent state and can be used to evaluate molecular changes associated with this process. At first, PSA levels drop and tumor volume decreases, but after a period of 60-120 days, regrowth of tumors is observed. LuCaP 35 has metastatic potential and results in mixed bone lesions. LuCaP 35 grown in intact male mice is androgen sensitive and responds to androgen withdrawal in the manner that is usually seen in patients.

LuCaP 35 cells were implanted subcutaneously into the flank of male SCID mice. When the tumors reached a volume of ca. 400 mm³, the mice were castrated and divided into three groups of 20 animals each. Group 1 controls received castration alone, Group 2 received castration and IMC-A12 intraperitoneally three times a week for 14 days starting 7 days after castration and Group 3 received IMC-A12 for 14 days beginning 14 days after castration. After 14 days of IMC-A12 no further therapy was administered. The timing of A12 administration for 2 weeks beginning either 1 or 2 weeks after castration was based on published data with the LuCaP 35 cell line indicating that maximum castration-induced apoptosis occurs within four days of castration (Corey, E. et al., 2003, Prostate 99:392-401). Since inhibition of IGF-IR signaling can cause cell cycle arrest and prevent cells from undergoing apoptosis, it was decided to start administration of A12 when apoptosis was "complete" following castration (Corey et al., 2003; Tennant, M. et al., 2003, Prostate, 56:115-22).

Blood samples were collected from orbital sinus weekly. The serum was separated and PSA levels were determined using the IMx Total PSA Assay (Abbott Laboratories, Abbott Park, Ill.). Tumors were measured twice weekly and tumor volume was estimated by the formula: volume=L×W2/2. Mice were sacrificed if tumors reached 1000 mm³ or when animal weight loss exceeded 20% of initial body weight. BrdU was injected i.p. into the mice 1 h before animals were sacrificed in order to determine in vivo tumor cell proliferation rate.

Upon castration, tumor growth was initially halted in all mice. (FIG. 1) In mice treated with IMC-A12, tumor volume decreased over the course of the study and there were no tumor specific deaths. In the untreated cohort, an increase in average tumor volume was evident by week 5, with tumor specific deaths (sacrificed) beginning in the fourth week and continuing through the study. Note that the plot of average tumor volume is artificially depressed for mice that did not receive IMC-A12 as each death removed a large tumor from the averaged tumor set.

Figure 2:
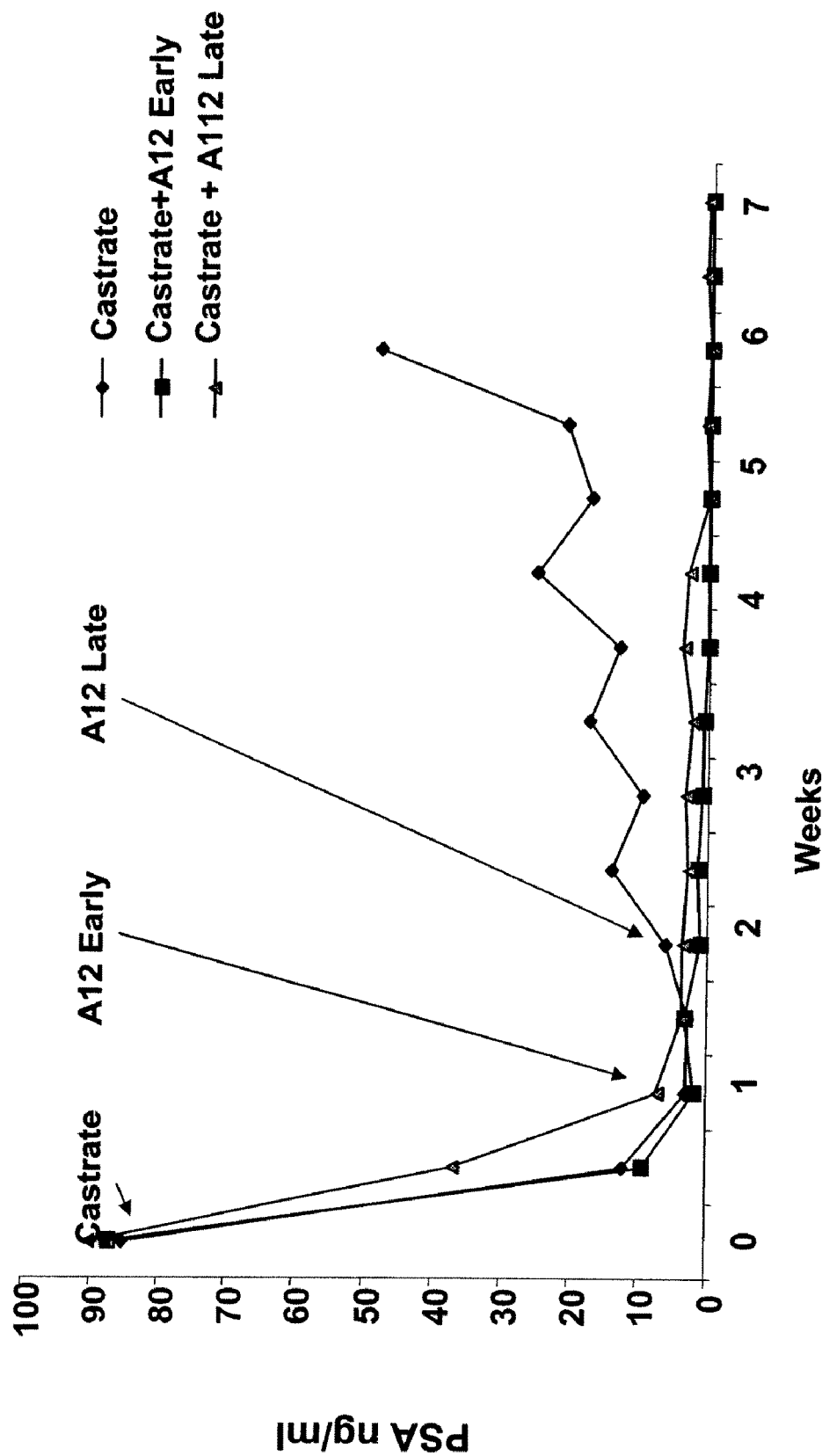
FIG. 2 depicts levels of PSA in the castrated control mice and in castrated mice treated with IMC-A12 starting one (early) or two (late) weeks after castration.

PSA levels were monitored in the LuCaP 35 xenograft mice. All mice responded initially to hormone ablation and a similar drop in PSA levels was observed in the first week following castration (FIG. 2). In mice treated by castration alone, after the initial drop, PSA levels then increased over the course of the study starting at about the second week. In contrast, PSA levels in castrated mice that were treated with IMC-A12 did not rise, but remained near baseline.

This study demonstrates that blocking IGF-IR signaling and expression after castration with IGF-IR antibody, IMC-A12, results in a significantly greater decrease in tumor volume than castration alone, p<0.001, and significantly prolongs the time to AI tumor regrowth as determined by tumor volume and an increase in PSA, p<0.001.

In control animals treated by castration alone, tumor growth stopped for about four weeks, but increased thereafter. Among animals treated by castration alone more than half were sacrificed due to tumor growth by 9 weeks following castration and most animals had been sacrificed by the end of 16 weeks. In contrast, all animals which received IMC-A12 were alive after 16 weeks.

The in vivo results presented demonstrate the effectiveness of inhibition of IGF-IR signal transduction. Notably, the IGF-IR antagonist was administered over the course of 14 days, and then halted. In a separate study in which A12 was administered in a similar manner, some tumor regrowth was observed late in the study following administration of A12. Two of 40 Group 2 and 3 animals had to be sacrificed because of tumor volume by the end of the study. Maintenance doses of an IGF-IR antagonist would prolong the time to tumor regrowth indefinitely.

Figure 5:
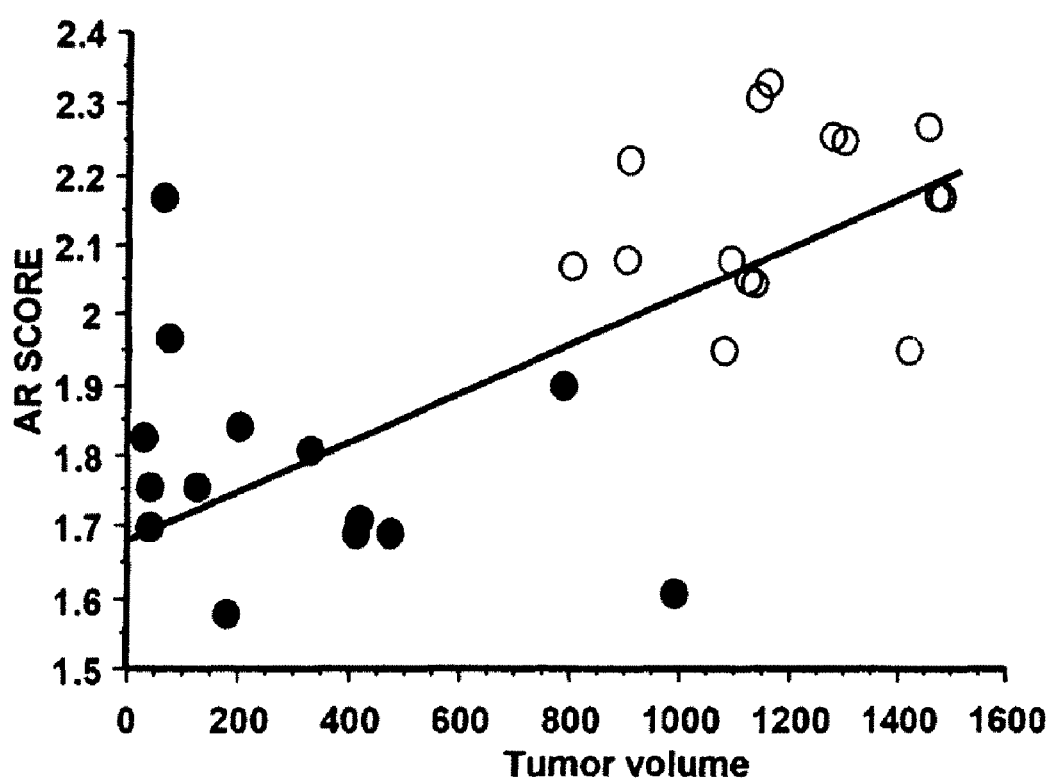
FIG. 5 depicts the correlation between AR score and tumor volume. R=0.66, p<0.01. Castrate only values are in the open circles and Castrate+A12 early and late values are in the closed circles. Values are the mean value for 100 nuclei graded per tumor.

To investigate whether there was a relationship between reduction in tumor volume in A12 treated tumors and AR translocation, AR immunohistochemistry was performed on tumors from each of the three groups, as shown in FIG. 5. A nuclear AR staining score was assigned to 100 nuclei from each tumor. Nuclei were scored blindly by two individuals and the mean of the two scores was counted as the score for that tissue. There is a significant positive correlation between tumor volume and nuclear AR intensity, r=0.66, p≦0.01.

Antagonism of IGF-IR Inhibits AR Translocation.

Figure 3:
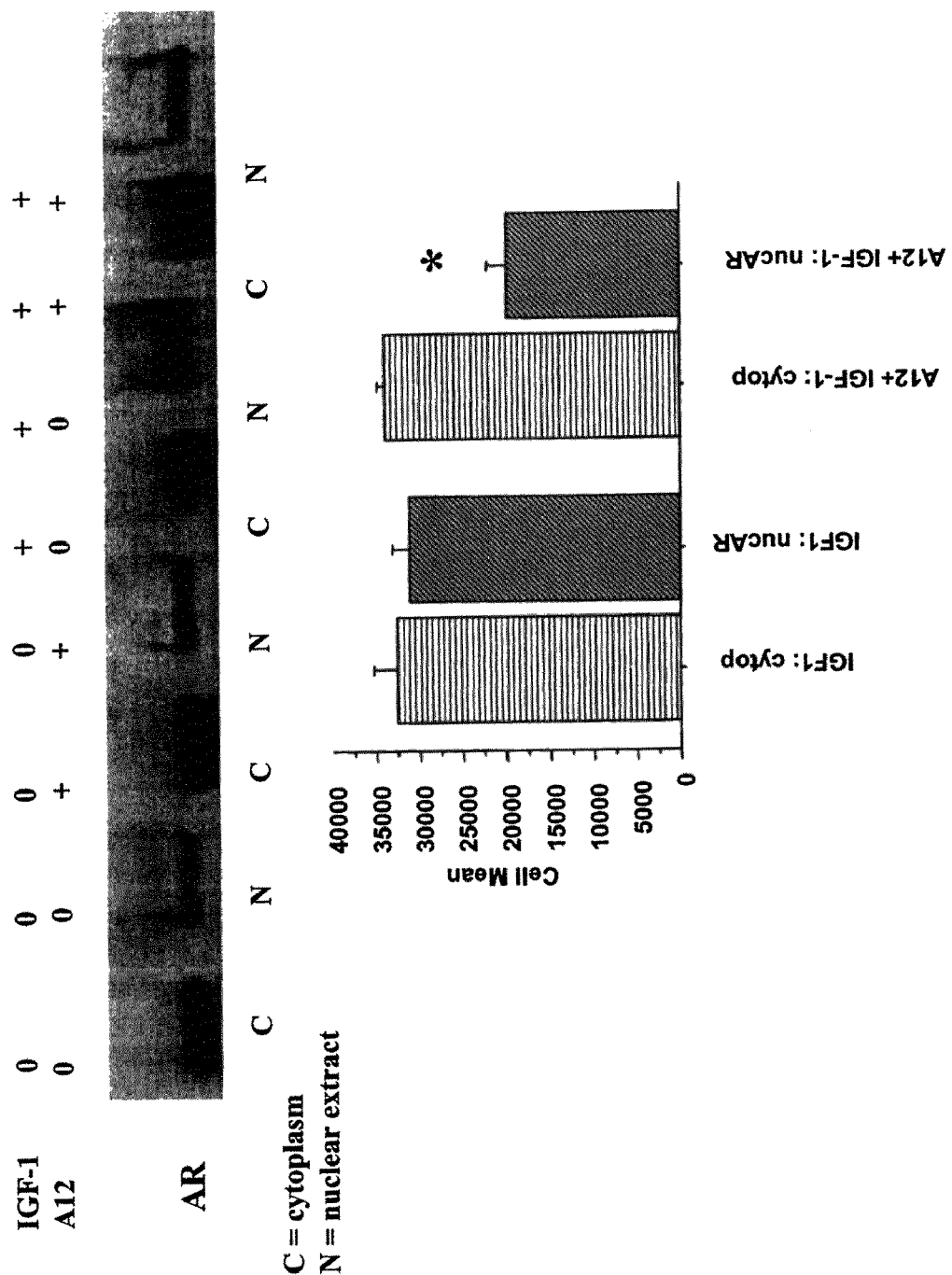
FIG. 3 depicts the distribution of androgen receptor (AR) in response to stimulation of IGF-IR with IGF and/or antagonism of IGF-IR with IMC-A12. Levels of cytoplasm and nuclear AR were assessed by Western Blots.

The effect of an stimulation and antagonism of IGF-IR on androgen receptor localization was assessed. LuCaP 35 cells were cultured with or without IGF-1 stimulation, in the presence of absence of IMC-A12. (FIG. 3) Cytoplasmic and nuclear extracts were prepared from treated cells and assessed by PAGE. The level of ERK was used to equalize loading of lanes. In cells stimulated with IGF-1, IMC-A12 caused a reduction in the proportion of androgen receptor observed in the nucleus.

Figure 4:
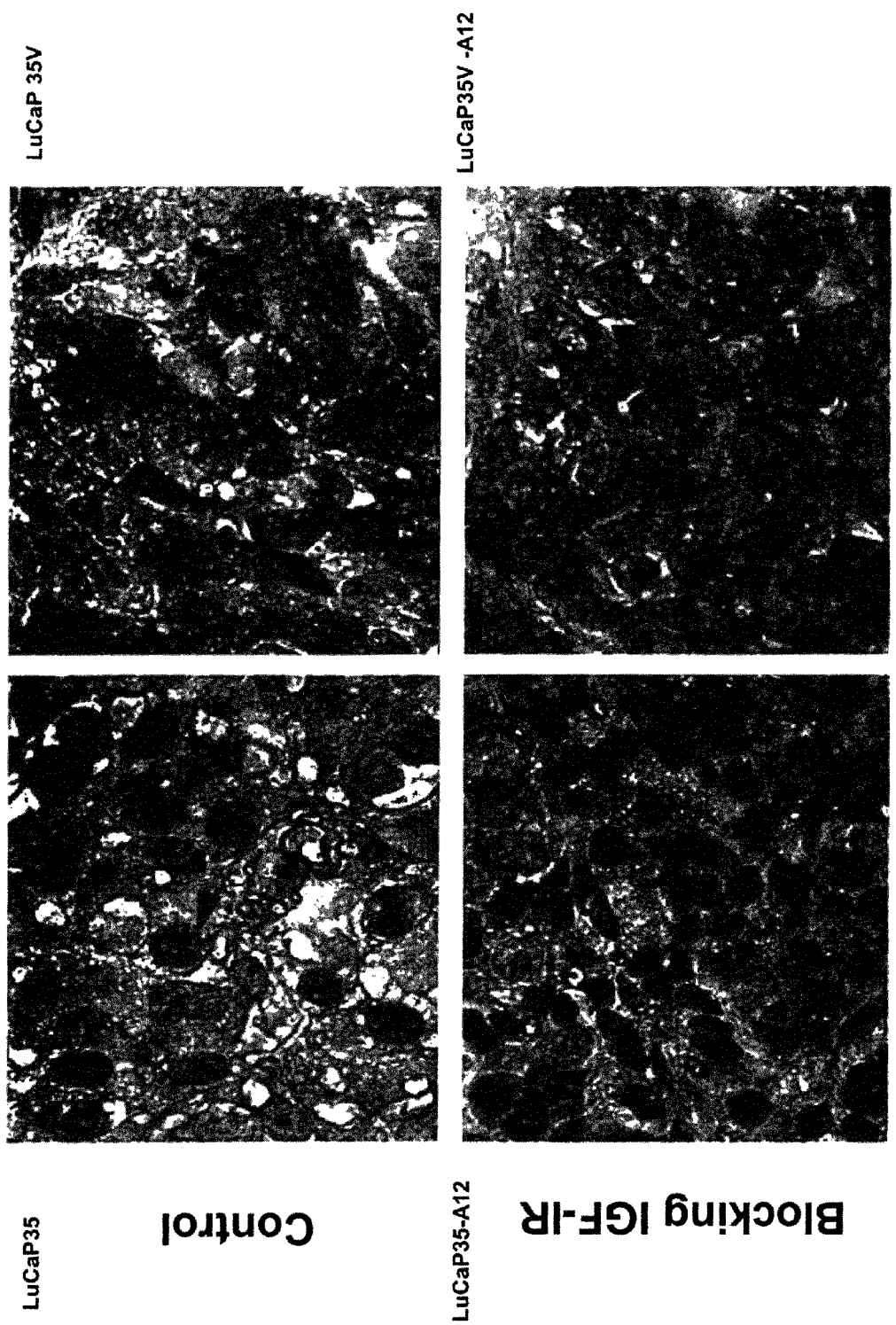
FIG. 4 depicts the effect of an IGF-IR antagonist (IMC-A12) on the distribution of androgen receptor (AR) in androgen dependent xenograft tumors of LuCaP 35 cells in intact mice (left column) and androgen independent xenograft tumors of LuCaP 35V cells in castrated mice (right column).

Androgen receptor translocation was also assessed by immunohistochemistry. (FIG. 4). LuCaP 35 (AD) xenograft tumors were grown in intact male and LuCaP 35V (AI) xenograft tumors were grown in castrated mice. Test mice were treated with IMC-A12. Serial sections of the tumors were prepared and stained with an AR specific antibody. In intact control mice, AR in androgen dependent LuCaP 35 tissue was localized predominantly in the nucleus. In tissue from test animals treated with IMC-A12, AR staining was observed in the cytoplasm. In castrated control mice, AR in androgen independent LuCaP 35 v cells was distributed between nucleus and cytoplasm. In tissue from test animals treated with IMC-A12, AR staining was predominantly in the cytoplasm.

In a similar experiment, the localization of AR was studied by fluorescence microscopy in tissue culture. Treatment with $10^{-8}$M DHT resulted in a significant redistribution of AR from cytoplasm to nucleus. Treatment with IGF-1 alone resulted in a partial redistribution of AR to the nucleus, and IMC-A12 completely reversed that effect.

Antagonism of IGF-IR Inhibits AR Dependent Gene Expression.

Survivin, which is an inhibitor of apoptosis, is strongly expressed in several human prostate cancer cell lines. In cell lines with intact androgen receptors, androgen stimulation with DHT increases survivin expression. Survivin expression is also observed to be mediated by AKT as IGF induced AKT signaling increases survivin expression even in AR-negative cell lines. A gene chip experiment to detect differential expression of survivin indicates that survivin expression is reduced upon treatment with IMC-A12.

Custom cDNA microarrays were constructed as previously described [ref] using clones derived from the Prostate Expression Data Base (PEDB), a sequence repository of human prostate expressed sequence tag (EST) data available to the public. (Nelson, P. S. et al., 2002, *Nucl. Acids Res.* 30:218-20). Methods of labeling with Cy3 and Cy5 fluorescent dyes, hybridization to the microarray slides, and array processing were as described (Tusher, V. et al., 2001, *Proc. Natl. Acad. Sci. U.S.A.* 98:5116-21).

Three tumors were pooled in each experimental group. To provide a reference standard RNA for use on cDNA microarrays, equal amounts of total RNA were isolated and pooled from LNCaP, DU145, PC3, and CWR22rV1 cell lines (American Type Culture Collection, Manassas, Va.) growing at log phase in dye-free RPMI-1640 medium supplemented with 10% fetal bovine serum (FBS; Life Technologies, Rockville, Md.). Total RNA was isolated from the pooled tumors and cell lines using Trizol (Invitrogen, SanDiego, Calif.). mRNA was amplified one round using the Ambion MessageAmp™ II Amplification Kit (Ambion Inc, Austin, Tex.), and sample quality and quantity were assessed by agarose gel electrophoresis and absorbance at A260. Hybridization probes were labeled and quality control of the array experiments was performed as described previously (Tusher, V. et al., 2001). Differences in gene expression associated with treatment groups were determined using the SAM procedure (Chu, G., Narasimhan, B., Tibshirani, R. & Tusher, V., 2002, Significance analysis of microarrays (sam) software, Stanford University) with a false discovery rate (FDR) of ≦10% considered significant (37). Similarities between samples were assessed by unsupervised, hierarchical clustering of genes and samples using Cluster 3.0 software (de Hoon et al., 2004, Bioinformatics 20:1453-4) and viewed by TreeView (Page, R. D., 1996, Comput. Appl. Biosci. 12:357-8).

Survivin and TUBB were also assayed by PCR using primers and methods previously described (Wu, J. et al., 2006, *Clin. Cancer Res.* 12:6153-60). A standard PCR fragment of the target cDNA was purified. A series of dilutions of the standards from 10 ng/µl to $10^{-3}$ pg/µl were used for real-time RT-PCR to generate the standard curves. One µg of total RNA from each group of pooled tumor was used for first-strand cDNA synthesis using Superscript First Strand Synthesis System (Invitrogen). Real-time RT-PCR was performed in 20 µl of reaction mixture consisted of 1 µl of first strand of cDNA, specific primers sets, and Lightcycler FastStart DNA Master Plus SYBR Green using a Roche Lightcycler following the manufacturer's protocol (Roche, Nutley, N.J.). RT-PCR products were subjected to melting curve analysis on Lightcycler software v3.5. The amplicon sizes were confirmed by agarose gel electrophoresis. Each sample was assayed in duplicate.

Figure 6:
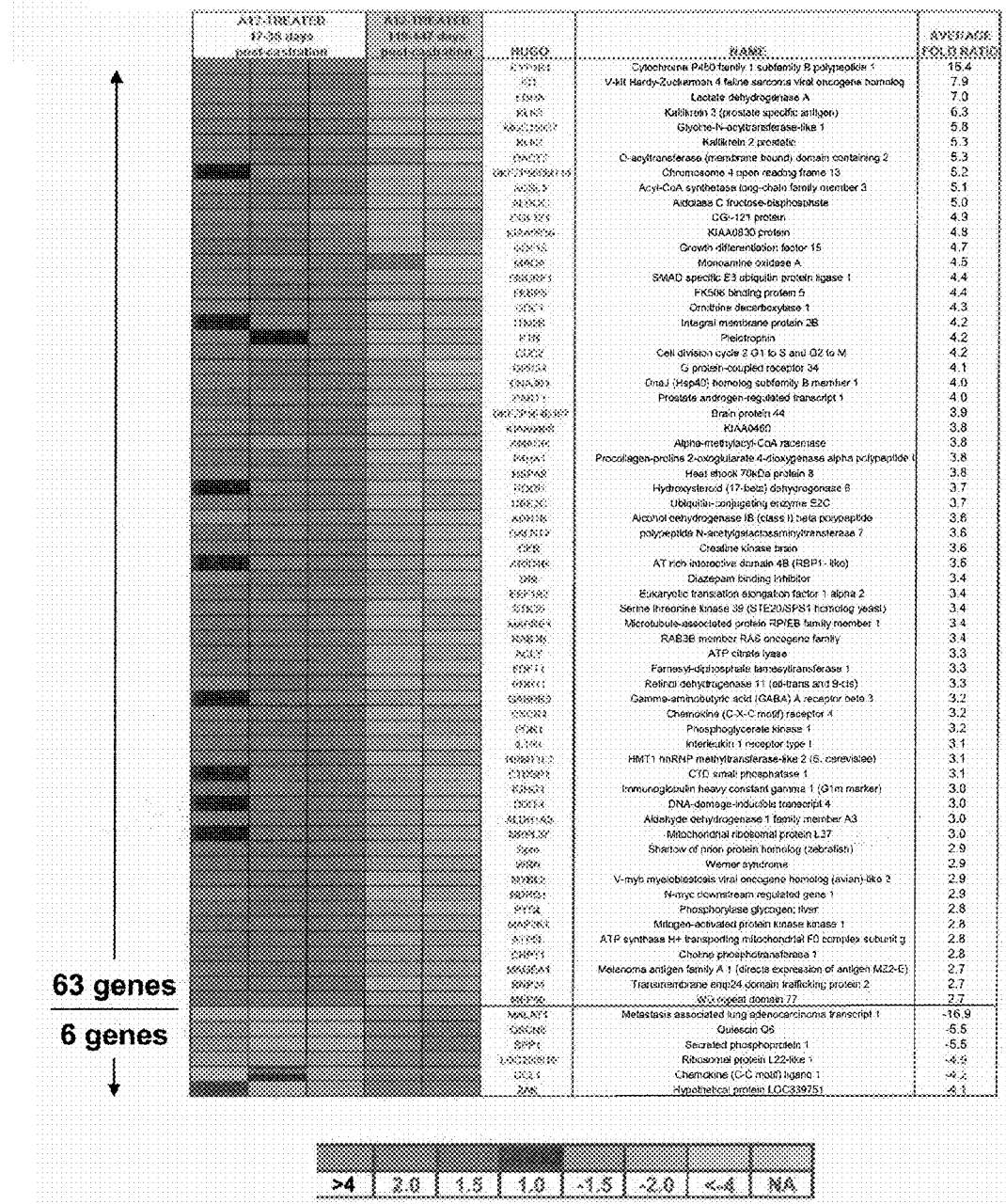
FIG. 6 depicts gene expression changes between two time periods for subcutaneous A12-treated tumors. Out of 3170 unique genes on the array with sufficient data to test, there were 21 up-regulated (including many androgen-regulated, denoted by "*") and 41 down-regulated with $\leq$10% q-value in the late time period when tumors began to recur compared to the early time period.

Castration combined with an IGF-IR antagonist is associated with a decrease in AR gene expression until recurrence of tumor. RNA samples from tumors harvested in each group at the time frames noted in Table 2 were analyzed on cDNA microarrays. No genes were found to be significantly altered between the time periods for group 1 (castration alone) when tested by two sample t-test in SAM (q-value≧100%) In addition, unsupervised, hierarchical clustering of known androgen-regulated genes did not segregate the two time periods. This may not be surprising since many of the animals in this group had PSA recurrence and increased nuclear AR scores compared to Groups 2 and 3 by day 40. In contrast, there were significant gene expression changes between the two time periods of A12-treated tumors. Out of 3170 unique genes on the array with sufficient data to test, there were 21 up-regulated (including many androgen-regulated) and 41 down-regulated with ≦10% q-value in the late time period when tumors began to recur compared to the early time period (FIG. 6) Furthermore, unsupervised, hierarchical clustering of known androgen-regulated genes clearly differentiated the A12-treated, two time periods into two separate clusters. These data indicate that nuclear AR expression is associated with AR transcriptional activity and prostate cancer progression through AR activation.

TABLE 2 cDNA Arrays at Each Time Point

| | Days Post Castration | |
|---|---|---|
| | 20-60 | 70-150 |
| Group 1 (castration) | 3 | 3 |
| Group 2 (castration + A12 early) | 2 | 2 |
| Group 3 (castration + A12 late) | 1 | 1 |

Figure 7:
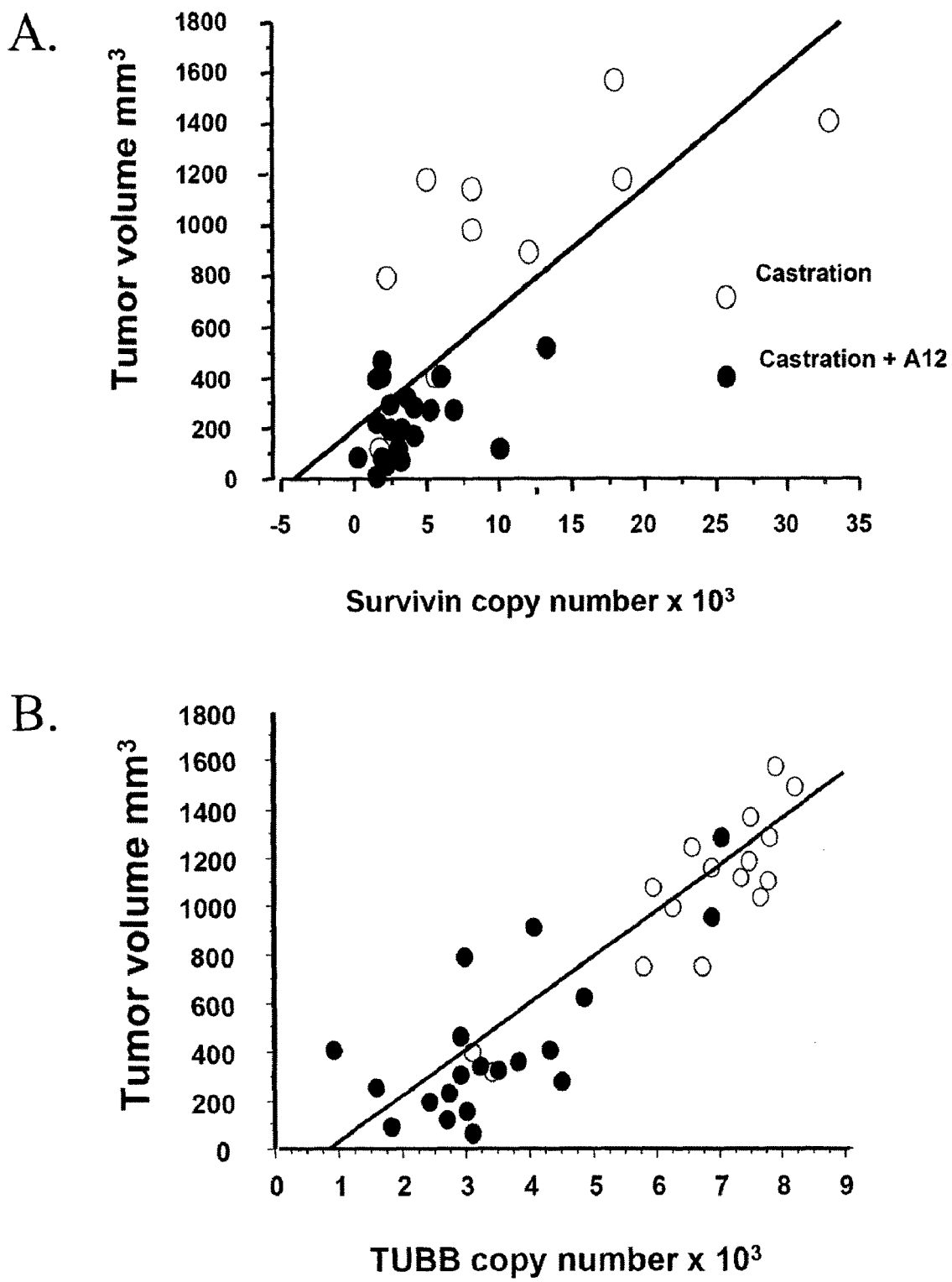
FIG. 7A depicts the correlation between survivin copy number score and tumor volume (r=0.66, p$\leq$0.01).
FIG. 7B depicts the correlation between tubulin beta peptide 3 copy number score and tumor volume (r=0.59, p$\leq$0.01). Castrate only values are in the open circles and Castrate+A12 early and late values are in the closed circles, Each value is the mean of three PCR runs.

Expression of survivin and β Tubulin is significantly decreased by an IGF-IR antagonist. The microarray studies determined that survivin expression was decreased in the tumors treated with A12 antibody. As depicted in FIG. 7A, Qt-RT PCR on RNA extracted from tumors demonstrates a significant positive correlation between survivin copy number and tumor volume, r=0.66, p≦0.01. A second gene recently implicated in IGF-IR induced tumor formation is β-tubulin, TUBB (O'Connor, R., 2003, *Horm. Metab. Res.* 35:771-7; Geller, J. et al., 1984, *J. Urol.* 132:693-700). TUBB was shown to be decreased in the microarrays and as shown in FIG. 7B, was shown in tumor specimens to correlate positively with tumor volume, r=0.59, p≦0.01, and to be significantly decreased in groups 2 and 3 compared to group 1. A third gene that was not different over time on the microarrays in group 1 but was decreased in the two early time periods in the group 2 and 3 animals was PSA. The change in PSA expression was confirmed by a similar pattern in the serum PSA levels.

Proliferation and Apoptosis

Apoptosis was determined by terminal deoxynucleotidyl transferase-mediated nick end labeling (TUNEL) assay and propidium (PI) staining using the Apop-Direct kit (BD Bio-Science) as previously described (Wu, J. D. et al., 2005, *Clin. Cancer Res.*, 11:3065-74). Briefly, 1×10⁶ cells from the single-cell suspension were fixed with 10% neutral buffer formalin (NBF) followed by 70% ethanol alcohol at −20° C. for 30 min. After several washes, cells were permeablized with 0.1% Triton X-100 and incubated with FITC-conjugated dUTP and terminal deoxynucleotidyl transferase enzyme −(TdT) at 37° C. for 1 h, followed by an incubation with PI/RNase buffer (100 µg/ml of PI, 50 µg/ml RNase ) at room temperature for 60 min. Samples were analyzed by flow cytometry using a BD FACscan. Data were analyzed with CellQuestPRO software. Apoptosis was also determined using by TUNNEL assay on formalin fixed tissue using the Apop-Tag kit (Millipore Co, MA) following manufacturer's recommendations. Apoptotic cells were determined per 300 cells per tissue slide.

As shown in Table 3, proliferation was significantly greater in the Group 1 tumors compared to Group 2 and 3, p≦0.01. In contrast, apoptosis as determined by TUNEL staining was higher in the Group 1 compared to Groups 2 and 3, Table 3.

TABLE 3

| Treatment Group | Apoptosis and BRDU Uptake | |
|---|---|---|
| | Apoptosis (TUNEL) +/− SEM | BRDU +/− SEM |
| Castrate | 6.58 +/− 1.41 | 27.74 +/− 1.93 |
| Castrate + A12 early | 1.29 +/− 0.49 ** | 17.78 +/− 2.74 ** |
| Castrate + A12 late | 1.16 +/− 0.37 ** | 12.36 +/− 1.75 ** |

** p < 0.001 compared to castrate group.

---

The invention claimed is:

1. A method of inhibiting transition of an androgen dependent cancer to an androgen independent cancer comprising administering an IGF-IR antagonist, wherein the IGF-IR antagonist is IMC-A12, and inhibiting growth of the androgen dependent cancer comprising administering androgen deprivation therapy.

2. The method of claim 1, wherein the androgen dependent cancer is prostate cancer.

3. The method of claim 1, wherein the androgen deprivation therapy and the IGF-IR antagonist are initiated at about the same time.

4. The method of claim 1, wherein the IGF-IR antagonist is initiated after the androgen deprivation therapy and before the androgen dependent cancer becomes androgen independent.

5. The method of claim 1, wherein the method of inhibiting growth of the androgen dependent cancer further comprises administering an IGF-IR antagonist.

6. The method of claim 1, wherein the androgen deprivation therapy comprises administering a luteinizing hormone-releasing hormone (LHRH) analog.

7. The method of claim 1, wherein the androgen deprivation therapy comprises administering anti-androgen treatment.

8. The method of claim 1, wherein the androgen deprivation therapy comprises administering an adrenal androgen inhibitor.

9. The method of claim 1, wherein the androgen deprivation therapy is orchiectomy.

10. The method of claim 1, wherein the androgen deprivation therapy and the IGF-IR antagonist are administered with an anti-neoplastic agent.

11. The method of claim 10, wherein the anti-neoplastic agent is radiation.

12. A method of inhibiting transition of an androgen dependent cancer to an androgen independent cancer comprising administering an IGF-IR antagonist, wherein the IGF-IR antagonist is IMC-A12.

13. The method of claim 12, wherein the androgen dependent cancer is prostate cancer.

* * * * *

SEQUENCE LISTING

```
<160> NUMBER OF SEQ ID NOS: 50

<210> SEQ ID NO 1
<211> LENGTH: 390
<212> TYPE: DNA
<213> ORGANISM: Homo sapiens
<220> FEATURE:
<221> NAME/KEY: CDS
<222> LOCATION: (1)..(390)

<400> SEQUENCE: 1 gag gtc cag ctg gtg cag tct ggg gct gag gtg aag aag cct ggg tcc      48
Glu Val Gln Leu Val Gln Ser Gly Ala Glu Val Lys Lys Pro Gly Ser
  1               5                  10                  15 tcg gtg aag gtc tcc tgc aag gct tct gga ggc acc ttc agc agc tat      96
Ser Val Lys Val Ser Cys Lys Ala Ser Gly Gly Thr Phe Ser Ser Tyr
             20                  25                  30 gct atc agc tgg gtg cga cag gcc cct gga caa ggg ctt gag tgg atg     144
Ala Ile Ser Trp Val Arg Gln Ala Pro Gly Gln Gly Leu Glu Trp Met
         35                  40                  45 gga ggg atc atc cct atc ttt ggt aca gca aac tac gca cag aag ttc     192
Gly Gly Ile Ile Pro Ile Phe Gly Thr Ala Asn Tyr Ala Gln Lys Phe
     50                  55                  60 cag ggc aga gtc acg att acc gcg gac aaa tcc acg agc aca gcc tac     240
Gln Gly Arg Val Thr Ile Thr Ala Asp Lys Ser Thr Ser Thr Ala Tyr
 65                  70                  75                  80 atg gag ctg agc agc ctg aga tct gag gac acg gcc gtg tat tac tgt     288
Met Glu Leu Ser Ser Leu Arg Ser Glu Asp Thr Ala Val Tyr Tyr Cys
                 85                  90                  95 gcg aga gcg cca tta cga ttt ttg gag tgg tcc acc caa gac cac tac     336
Ala Arg Ala Pro Leu Arg Phe Leu Glu Trp Ser Thr Gln Asp His Tyr
            100                 105                 110 tac tac tac tac atg gac gtc tgg ggc aaa ggg acc acg gtc acc gtc     384
Tyr Tyr Tyr Tyr Met Asp Val Trp Gly Lys Gly Thr Thr Val Thr Val
```

```
tca agc                                                                      390
Ser Ser
    130

<210> SEQ ID NO 2
<211> LENGTH: 130
<212> TYPE: PRT
<213> ORGANISM: Homo sapiens

<400> SEQUENCE: 2

Glu Val Gln Leu Val Gln Ser Gly Ala Glu Val Lys Lys Pro Gly Ser
1               5                  10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Pro Leu Arg Phe Leu Glu Trp Ser Thr Gln Asp His Tyr
            100                 105                 110

Tyr Tyr Tyr Tyr Met Asp Val Trp Gly Lys Gly Thr Thr Val Thr Val
        115                 120                 125

Ser Ser
    130

<210> SEQ ID NO 3
<211> LENGTH: 1440
<212> TYPE: DNA
<213> ORGANISM: Homo sapiens
<220> FEATURE:
<221> NAME/KEY: CDS
<222> LOCATION: (1)..(1437)

<400> SEQUENCE: 3 atg gga tgg tca tgt atc atc ctt ttt cta gta gca act gca act gga    48
Met Gly Trp Ser Cys Ile Ile Leu Phe Leu Val Ala Thr Ala Thr Gly
1               5                  10                  15 gta cat tca gag gtc cag ctg gtg cag tct ggg gct gag gtg aag aag    96
Val His Ser Glu Val Gln Leu Val Gln Ser Gly Ala Glu Val Lys Lys
            20                  25                  30 cct ggg tcc tcg gtg aag gtc tcc tgc aag gct tct gga ggc acc ttc   144
Pro Gly Ser Ser Val Lys Val Ser Cys Lys Ala Ser Gly Gly Thr Phe
        35                  40                  45 agc agc tat gct atc agc tgg gtg cga cag gcc cct gga caa ggg ctt   192
Ser Ser Tyr Ala Ile Ser Trp Val Arg Gln Ala Pro Gly Gln Gly Leu
    50                  55                  60 gag tgg atg gga ggg atc atc cct atc ttt ggt aca gca aac tac gca   240
Glu Trp Met Gly Gly Ile Ile Pro Ile Phe Gly Thr Ala Asn Tyr Ala
65                  70                  75                  80 cag aag ttc cag ggc aga gtc acg att acc gcg gac aaa tcc acg agc   288
Gln Lys Phe Gln Gly Arg Val Thr Ile Thr Ala Asp Lys Ser Thr Ser
                85                  90                  95 aca gcc tac atg gag ctg agc agc ctg aga tct gag gac acg gcc gtg   336
Thr Ala Tyr Met Glu Leu Ser Ser Leu Arg Ser Glu Asp Thr Ala Val
            100                 105                 110
```

```
tat tac tgt gcg aga gcg cca tta cga ttt ttg gag tgg tcc acc caa      384
Tyr Tyr Cys Ala Arg Ala Pro Leu Arg Phe Leu Glu Trp Ser Thr Gln
            115                 120                 125 gac cac tac tac tac tac tac atg gac gtc tgg ggc aaa ggg acc acg      432
Asp His Tyr Tyr Tyr Tyr Tyr Met Asp Val Trp Gly Lys Gly Thr Thr
        130                 135                 140 gtc acc gtc tca agc gcc tcc acc aag ggc cca tcg gtc ttc ccc ctg      480
Val Thr Val Ser Ser Ala Ser Thr Lys Gly Pro Ser Val Phe Pro Leu
145                 150                 155                 160 gca ccc tcc tcc aag agc acc tct ggg ggc aca gcg gcc ctg ggc tgc      528
Ala Pro Ser Ser Lys Ser Thr Ser Gly Gly Thr Ala Ala Leu Gly Cys
                165                 170                 175 ctg gtc aag gac tac ttc ccc gaa ccg gtg acg gtg tcg tgg aac tca      576
Leu Val Lys Asp Tyr Phe Pro Glu Pro Val Thr Val Ser Trp Asn Ser
            180                 185                 190 ggc gcc ctg acc agc ggc gtg cac acc ttc ccg gct gtc cta cag tcc      624
Gly Ala Leu Thr Ser Gly Val His Thr Phe Pro Ala Val Leu Gln Ser
        195                 200                 205 tca gga ctc tac tcc ctc agc agc gtg gtg acc gtg ccc tcc agc agc      672
Ser Gly Leu Tyr Ser Leu Ser Ser Val Val Thr Val Pro Ser Ser Ser
    210                 215                 220 ttg ggc acc cag acc tac atc tgc aac gtg aat cac aag ccc agc aac      720
Leu Gly Thr Gln Thr Tyr Ile Cys Asn Val Asn His Lys Pro Ser Asn
225                 230                 235                 240 acc aag gtg gac aag aaa gtt gag ccc aaa tct tgt gac aaa act cac      768
Thr Lys Val Asp Lys Lys Val Glu Pro Lys Ser Cys Asp Lys Thr His
                245                 250                 255 aca tgc cca ccg tgc cca gca cct gaa ctc ctg ggg gga ccg tca gtc      816
Thr Cys Pro Pro Cys Pro Ala Pro Glu Leu Leu Gly Gly Pro Ser Val
            260                 265                 270 ttc ctc ttc ccc cca aaa ccc aag gac acc ctc atg atc tcc cgg acc      864
Phe Leu Phe Pro Pro Lys Pro Lys Asp Thr Leu Met Ile Ser Arg Thr
        275                 280                 285 cct gag gtc aca tgc gtg gtg gtg gac gtg agc cac gaa gac cct gag      912
Pro Glu Val Thr Cys Val Val Val Asp Val Ser His Glu Asp Pro Glu
    290                 295                 300 gtc aag ttc aac tgg tac gtg gac ggc gtg gag gtg cat aat gcc aag      960
Val Lys Phe Asn Trp Tyr Val Asp Gly Val Glu Val His Asn Ala Lys
305                 310                 315                 320 aca aag ccg cgg gag gag cag tac aac agc acg tac cgg gtg gtc agc     1008
Thr Lys Pro Arg Glu Glu Gln Tyr Asn Ser Thr Tyr Arg Val Val Ser
                325                 330                 335 gtc ctc acc gtc ctg cac cag gac tgg ctg aat ggc aag gag tac aag     1056
Val Leu Thr Val Leu His Gln Asp Trp Leu Asn Gly Lys Glu Tyr Lys
            340                 345                 350 tgc aag gtc tcc aac aaa gcc ctc cca gcc ccc atc gag aaa acc atc     1104
Cys Lys Val Ser Asn Lys Ala Leu Pro Ala Pro Ile Glu Lys Thr Ile
        355                 360                 365 tcc aaa gcc aaa ggg cag ccc cga gaa cca cag gtg tac acc ctg ccc     1152
Ser Lys Ala Lys Gly Gln Pro Arg Glu Pro Gln Val Tyr Thr Leu Pro
    370                 375                 380 cca tcc cgg gag gag atg acc aag aac cag gtc agc ctg acc tgc ctg     1200
Pro Ser Arg Glu Glu Met Thr Lys Asn Gln Val Ser Leu Thr Cys Leu
385                 390                 395                 400 gtc aaa ggc ttc tat ccc agc gac atc gcc gtg gag tgg gag agc aat     1248
Val Lys Gly Phe Tyr Pro Ser Asp Ile Ala Val Glu Trp Glu Ser Asn
                405                 410                 415 ggg cag ccg gag aac aac tac aag acc acg cct ccc gtg ctg gac tcc     1296
Gly Gln Pro Glu Asn Asn Tyr Lys Thr Thr Pro Pro Val Leu Asp Ser
            420                 425                 430
```

```
gac ggc tcc ttc ttc ctc tac agc aag ctc acc gtg gac aag agc agg    1344
Asp Gly Ser Phe Phe Leu Tyr Ser Lys Leu Thr Val Asp Lys Ser Arg
        435                 440                 445 tgg cag cag ggg aac gtc ttc tca tgc tcc gtg atg cat gag gct ctg    1392
Trp Gln Gln Gly Asn Val Phe Ser Cys Ser Val Met His Glu Ala Leu
450                 455                 460 cac aac cac tac acg cag aag agc ctc tcc ctg tct ccg ggt aaa tga    1440
His Asn His Tyr Thr Gln Lys Ser Leu Ser Leu Ser Pro Gly Lys
465                 470                 475

<210> SEQ ID NO 4
<211> LENGTH: 479
<212> TYPE: PRT
<213> ORGANISM: Homo sapiens

<400> SEQUENCE: 4

Met Gly Trp Ser Cys Ile Ile Leu Phe Leu Val Ala Thr Ala Thr Gly
1               5                   10                  15

Val His Ser Glu Val Gln Leu Val Gln Ser Gly Ala Glu Val Lys Lys
            20                  25                  30

Pro Gly Ser Ser Val Lys Val Ser Cys Lys Ala Ser Gly Gly Thr Phe
        35                  40                  45

Ser Ser Tyr Ala Ile Ser Trp Val Arg Gln Ala Pro Gly Gln Gly Leu
    50                  55                  60

Glu Trp Met Gly Gly Ile Ile Pro Ile Phe Gly Thr Ala Asn Tyr Ala
65                  70                  75                  80

Gln Lys Phe Gln Gly Arg Val Thr Ile Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Ala Pro Leu Arg Phe Leu Glu Trp Ser Thr Gln
        115                 120                 125

Asp His Tyr Tyr Tyr Tyr Met Asp Val Trp Gly Lys Gly Thr Thr
    130                 135                 140

Val Thr Val Ser Ser Ala Ser Thr Lys Gly Pro Ser Val Phe Pro Leu
145                 150                 155                 160

Ala Pro Ser Ser Lys Ser Thr Ser Gly Gly Thr Ala Ala Leu Gly Cys
                165                 170                 175

Leu Val Lys Asp Tyr Phe Pro Glu Pro Val Thr Val Ser Trp Asn Ser
            180                 185                 190

Gly Ala Leu Thr Ser Gly Val His Thr Phe Pro Ala Val Leu Gln Ser
        195                 200                 205

Ser Gly Leu Tyr Ser Leu Ser Ser Val Val Thr Val Pro Ser Ser Ser
    210                 215                 220

Leu Gly Thr Gln Thr Tyr Ile Cys Asn Val Asn His Lys Pro Ser Asn
225                 230                 235                 240

Thr Lys Val Asp Lys Lys Val Glu Pro Lys Ser Cys Asp Lys Thr His
                245                 250                 255

Thr Cys Pro Pro Cys Pro Ala Pro Glu Leu Leu Gly Gly Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
    290                 295                 300

Val Lys Phe Asn Trp Tyr Val Asp Gly Val Glu Val His Asn Ala Lys
305                 310                 315                 320
```

```
Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Arg Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Lys
465                 470                 475

<210> SEQ ID NO 5
<211> LENGTH: 327
<212> TYPE: DNA
<213> ORGANISM: Homo sapiens
<220> FEATURE:
<221> NAME/KEY: CDS
<222> LOCATION: (1)..(327)

<400> SEQUENCE: 5 tct tct gag ctg act cag gac cct gct gtg tct gtg gcc ttg gga cag     48
Ser Ser Glu Leu Thr Gln Asp Pro Ala Val Ser Val Ala Leu Gly Gln
  1               5                  10                  15 aca gtc agg atc aca tgc caa gga gac agc ctc aga agc tat tat gca    96
Thr Val Arg Ile Thr Cys Gln Gly Asp Ser Leu Arg Ser Tyr Tyr Ala
                 20                  25                  30 agc tgg tac cag cag aag cca gga cag gcc cct gta ctt gtc atc tat   144
Ser Trp Tyr Gln Gln Lys Pro Gly Gln Ala Pro Val Leu Val Ile Tyr
             35                  40                  45 ggt aaa aac aac cgg ccc tca ggg atc cca gac cga ttc tct ggc tcc   192
Gly Lys Asn Asn Arg Pro Ser Gly Ile Pro Asp Arg Phe Ser Gly Ser
         50                  55                  60 agc tca gga aac aca gct tcc ttg acc atc act ggg gct cag gcg gaa   240
Ser Ser Gly Asn Thr Ala Ser Leu Thr Ile Thr Gly Ala Gln Ala Glu
 65                  70                  75                  80 gat gag gct gac tat tac tgt aac tcc cgg gac aac agt gat aac cgt   288
Asp Glu Ala Asp Tyr Tyr Cys Asn Ser Arg Asp Asn Ser Asp Asn Arg
                 85                  90                  95 ctg ata ttt ggc ggc ggg acc aag ctg acc gtc ctc agt                327
Leu Ile Phe Gly Gly Gly Thr Lys Leu Thr Val Leu Ser
            100                 105

<210> SEQ ID NO 6
<211> LENGTH: 109
<212> TYPE: PRT
<213> ORGANISM: Homo sapiens

<400> SEQUENCE: 6

Ser Ser Glu Leu Thr Gln Asp Pro Ala Val Ser Val Ala Leu Gly Gln
  1               5                  10                  15
```

```
            Thr Val Arg Ile Thr Cys Gln Gly Asp Ser Leu Arg Ser Tyr Tyr Ala
                        20                  25                  30

Ser Trp Tyr Gln Gln Lys Pro Gly Gln Ala Pro Val Leu Val Ile Tyr
                    35                  40                  45

Gly Lys Asn Asn Arg Pro Ser Gly Ile Pro Asp Arg Phe Ser Gly Ser
                50                  55                  60

Ser Ser Gly Asn Thr Ala Ser Leu Thr Ile Thr Gly Ala Gln Ala Glu
             65                  70                  75                  80

Asp Glu Ala Asp Tyr Tyr Cys Asn Ser Arg Asp Ser Asp Asn Arg
                            85                  90                  95

Leu Ile Phe Gly Gly Gly Thr Lys Leu Thr Val Leu Ser
                        100                 105

<210> SEQ ID NO 7
<211> LENGTH: 702
<212> TYPE: DNA
<213> ORGANISM: Homo sapiens
<220> FEATURE:
<221> NAME/KEY: CDS
<222> LOCATION: (1)..(699)

<400> SEQUENCE: 7 atg gga tgg tca tgt atc atc ctt ttt cta gta gca act gca act gga      48
Met Gly Trp Ser Cys Ile Ile Leu Phe Leu Val Ala Thr Ala Thr Gly
 1               5                  10                  15 gta cat tca tct tct gag ctg act cag gac cct gct gtg tct gtg gcc      96
Val His Ser Ser Ser Glu Leu Thr Gln Asp Pro Ala Val Ser Val Ala
                20                  25                  30 ttg gga cag aca gtc agg atc aca tgc caa gga gac agc ctc aga agc     144
Leu Gly Gln Thr Val Arg Ile Thr Cys Gln Gly Asp Ser Leu Arg Ser
            35                  40                  45 tat tat gca agc tgg tac cag cag aag cca gga cag gcc cct gta ctt     192
Tyr Tyr Ala Ser Trp Tyr Gln Gln Lys Pro Gly Gln Ala Pro Val Leu
        50                  55                  60 gtc atc tat ggt aaa aac aac cgg ccc tca ggg atc cca gac cga ttc     240
Val Ile Tyr Gly Lys Asn Asn Arg Pro Ser Gly Ile Pro Asp Arg Phe
 65                  70                  75                  80 tct ggc tcc agc tca gga aac aca gct tcc ttg acc atc act ggg gct     288
Ser Gly Ser Ser Ser Gly Asn Thr Ala Ser Leu Thr Ile Thr Gly Ala
                85                  90                  95 cag gcg gaa gat gag gct gac tat tac tgt aac tcc cgg gac aac agt     336
Gln Ala Glu Asp Glu Ala Asp Tyr Tyr Cys Asn Ser Arg Asp Asn Ser
            100                 105                 110 gat aac cgt ctg ata ttt ggc ggc ggg acc aag ctg acc gtc ctc agt     384
Asp Asn Arg Leu Ile Phe Gly Gly Gly Thr Lys Leu Thr Val Leu Ser
        115                 120                 125 cag ccc aag gct gcc ccc tcg gtc act ctg ttc ccg ccc tcc tct gag     432
Gln Pro Lys Ala Ala Pro Ser Val Thr Leu Phe Pro Pro Ser Ser Glu
    130                 135                 140 gag ctt caa gcc aac aag gcc aca ctg gtg tgt ctc ata agt gac ttc     480
Glu Leu Gln Ala Asn Lys Ala Thr Leu Val Cys Leu Ile Ser Asp Phe
145                 150                 155                 160 tac ccg gga gcc gtg aca gtg gcc tgg aag gca gat agc agc ccc gtc     528
Tyr Pro Gly Ala Val Thr Val Ala Trp Lys Ala Asp Ser Ser Pro Val
                165                 170                 175 aag gcg gga gtg gag acc acc aca ccc tcc aaa caa agc aac aac aag     576
Lys Ala Gly Val Glu Thr Thr Thr Pro Ser Lys Gln Ser Asn Asn Lys
            180                 185                 190 tac gcg gcc agc agc tat ctg agc ctg acg cct gag cag tgg aag tcc     624
Tyr Ala Ala Ser Ser Tyr Leu Ser Leu Thr Pro Glu Gln Trp Lys Ser
        195                 200                 205
```

```
cac aga agc tac agc tgc cag gtc acg cat gaa ggg agc acc gtg gag     672
His Arg Ser Tyr Ser Cys Gln Val Thr His Glu Gly Ser Thr Val Glu
    210                 215                 220 aag aca gtg gcc cct gca gaa tgc tct tga                             702
Lys Thr Val Ala Pro Ala Glu Cys Ser
225                 230

<210> SEQ ID NO 8
<211> LENGTH: 233
<212> TYPE: PRT
<213> ORGANISM: Homo sapiens

<400> SEQUENCE: 8

Met Gly Trp Ser Cys Ile Ile Leu Phe Leu Val Ala Thr Ala Thr Gly
 1               5                  10                  15

Val His Ser Ser Ser Glu Leu Thr Gln Asp Pro Ala Val Ser Val Ala
                20                  25                  30

Leu Gly Gln Thr Val Arg Ile Thr Cys Gln Gly Asp Ser Leu Arg Ser
            35                  40                  45

Tyr Tyr Ala Ser Trp Tyr Gln Gln Lys Pro Gly Gln Ala Pro Val Leu
        50                  55                  60

Val Ile Tyr Gly Lys Asn Asn Arg Pro Ser Gly Ile Pro Asp Arg Phe
 65                 70                  75                  80

Ser Gly Ser Ser Ser Gly Asn Thr Ala Ser Leu Thr Ile Thr Gly Ala
                85                  90                  95

Gln Ala Glu Asp Glu Ala Asp Tyr Tyr Cys Asn Ser Arg Asp Asn Ser
            100                 105                 110

Asp Asn Arg Leu Ile Phe Gly Gly Gly Thr Lys Leu Thr Val Leu Ser
        115                 120                 125

Gln Pro Lys Ala Ala Pro Ser Val Thr Leu Phe Pro Pro Ser Ser Glu
130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Ala Glu Cys Ser
225                 230

<210> SEQ ID NO 9
<211> LENGTH: 327
<212> TYPE: DNA
<213> ORGANISM: Homo sapiens
<220> FEATURE:
<221> NAME/KEY: CDS
<222> LOCATION: (1)..(327)

<400> SEQUENCE: 9 tct tct gag ctg act cag gac cct gct gtg tct gtg gcc ttg gga cag    48
Ser Ser Glu Leu Thr Gln Asp Pro Ala Val Ser Val Ala Leu Gly Gln
 1               5                  10                  15 aca gtc agg atc aca tgc caa gga gac agc ctc aga agc tat tat gca    96
Thr Val Arg Ile Thr Cys Gln Gly Asp Ser Leu Arg Ser Tyr Tyr Ala
                20                  25                  30
```

```
acc tgg tac cag cag aag cca gga cag gcc cct att ctt gtc atc tat      144
Thr Trp Tyr Gln Gln Lys Pro Gly Gln Ala Pro Ile Leu Val Ile Tyr
         35                  40                  45 ggt gaa aat aag cgg ccc tca ggg atc cca gac cga ttc tct ggc tcc      192
Gly Glu Asn Lys Arg Pro Ser Gly Ile Pro Asp Arg Phe Ser Gly Ser
 50                  55                  60 agc tca gga aac aca gct tcc ttg acc atc act ggg gct cag gca gaa      240
Ser Ser Gly Asn Thr Ala Ser Leu Thr Ile Thr Gly Ala Gln Ala Glu
 65                  70                  75                  80 gat gag gct gac tac tat tgt aaa tct cgg gat ggc agt ggt caa cat      288
Asp Glu Ala Asp Tyr Tyr Cys Lys Ser Arg Asp Gly Ser Gly Gln His
                 85                  90                  95 ctg gtg ttc ggc gga ggg acc aag ctg acc gtc cta ggt              327
Leu Val Phe Gly Gly Gly Thr Lys Leu Thr Val Leu Gly
                100                 105

<210> SEQ ID NO 10
<211> LENGTH: 109
<212> TYPE: PRT
<213> ORGANISM: Homo sapiens

<400> SEQUENCE: 10

Ser Ser Glu Leu Thr Gln Asp Pro Ala Val Ser Val Ala Leu Gly Gln
  1               5                  10                  15

Thr Val Arg Ile Thr Cys Gln Gly Asp Ser Leu Arg Ser Tyr Tyr Ala
                 20                  25                  30

Thr Trp Tyr Gln Gln Lys Pro Gly Gln Ala Pro Ile Leu Val Ile Tyr
             35                  40                  45

Gly Glu Asn Lys Arg Pro Ser Gly Ile Pro Asp Arg Phe Ser Gly Ser
 50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Lys Ser Arg Asp Gly Ser Gly Gln His
                 85                  90                  95

Leu Val Phe Gly Gly Gly Thr Lys Leu Thr Val Leu Gly
                100                 105

<210> SEQ ID NO 11
<211> LENGTH: 702
<212> TYPE: DNA
<213> ORGANISM: Homo sapiens
<220> FEATURE:
<221> NAME/KEY: CDS
<222> LOCATION: (1)..(699)

<400> SEQUENCE: 11 atg gga tgg tca tgt atc atc ctt ttt cta gta gca act gca act gga       48
Met Gly Trp Ser Cys Ile Ile Leu Phe Leu Val Ala Thr Ala Thr Gly
  1               5                  10                  15 gta cat tca tct tct gag ctg act cag gac cct gct gtg tct gtg gcc       96
Val His Ser Ser Ser Glu Leu Thr Gln Asp Pro Ala Val Ser Val Ala
                 20                  25                  30 ttg gga cag aca gtc agg atc aca tgc caa gga gac agc ctc aga agc      144
Leu Gly Gln Thr Val Arg Ile Thr Cys Gln Gly Asp Ser Leu Arg Ser
             35                  40                  45 tat tat gca acc tgg tac cag cag aag cca gga cag gcc cct att ctt      192
Tyr Tyr Ala Thr Trp Tyr Gln Gln Lys Pro Gly Gln Ala Pro Ile Leu
 50                  55                  60 gtc atc tat ggt gaa aat aag cgg ccc tca ggg atc cca gac cga ttc      240
Val Ile Tyr Gly Glu Asn Lys Arg Pro Ser Gly Ile Pro Asp Arg Phe
 65                  70                  75                  80
```

```
tct ggc tcc agc tca gga aac aca gct tcc ttg acc atc act ggg gct      288
Ser Gly Ser Ser Ser Gly Asn Thr Ala Ser Leu Thr Ile Thr Gly Ala
                85                  90                  95 cag gca gaa gat gag gct gac tac tat tgt aaa tct cgg gat ggc agt      336
Gln Ala Glu Asp Glu Ala Asp Tyr Tyr Cys Lys Ser Arg Asp Gly Ser
            100                 105                 110 ggt caa cat ctg gtg ttc ggc gga ggg acc aag ctg acc gtc cta ggt      384
Gly Gln His Leu Val Phe Gly Gly Gly Thr Lys Leu Thr Val Leu Gly
        115                 120                 125 cag ccc aag gct gcc ccc tcg gtc act ctg ttc ccg ccc tcc tct gag      432
Gln Pro Lys Ala Ala Pro Ser Val Thr Leu Phe Pro Pro Ser Ser Glu
    130                 135                 140 gag ctt caa gcc aac aag gcc aca ctg gtg tgt ctc ata agt gac ttc      480
Glu Leu Gln Ala Asn Lys Ala Thr Leu Val Cys Leu Ile Ser Asp Phe
145                 150                 155                 160 tac ccg gga gcc gtg aca gtg gcc tgg aag gca gat agc agc ccc gtc      528
Tyr Pro Gly Ala Val Thr Val Ala Trp Lys Ala Asp Ser Ser Pro Val
                165                 170                 175 aag gcg gga gtg gag acc acc aca ccc tcc aaa caa agc aac aac aag      576
Lys Ala Gly Val Glu Thr Thr Thr Pro Ser Lys Gln Ser Asn Asn Lys
            180                 185                 190 tac gcg gcc agc agc tat ctg agc ctg acg cct gag cag tgg aag tcc      624
Tyr Ala Ala Ser Ser Tyr Leu Ser Leu Thr Pro Glu Gln Trp Lys Ser
        195                 200                 205 cac aga agc tac agc tgc cag gtc acg cat gaa ggg agc acc gtg gag      672
His Arg Ser Tyr Ser Cys Gln Val Thr His Glu Gly Ser Thr Val Glu
    210                 215                 220 aag aca gtg gcc cct gca gaa tgc tct tga                              702
Lys Thr Val Ala Pro Ala Glu Cys Ser
225                 230

<210> SEQ ID NO 12
<211> LENGTH: 233
<212> TYPE: PRT
<213> ORGANISM: Homo sapiens

<400> SEQUENCE: 12

Met Gly Trp Ser Cys Ile Ile Leu Phe Leu Val Ala Thr Ala Thr Gly
1               5                   10                  15

Val His Ser Ser Glu Leu Thr Gln Asp Pro Ala Val Ser Val Ala
            20                  25                  30

Leu Gly Gln Thr Val Arg Ile Thr Cys Gln Gly Asp Ser Leu Arg Ser
        35                  40                  45

Tyr Tyr Ala Thr Trp Tyr Gln Gln Lys Pro Gly Gln Ala Pro Ile Leu
    50                  55                  60

Val Ile Tyr Gly Glu Asn Lys Arg Pro Ser Gly Ile Pro Asp Arg Phe
65                  70                  75                  80

Ser Gly Ser Ser Ser Gly Asn Thr Ala Ser Leu Thr Ile Thr Gly Ala
                85                  90                  95

Gln Ala Glu Asp Glu Ala Asp Tyr Tyr Cys Lys Ser Arg Asp Gly Ser
            100                 105                 110

Gly Gln His Leu Val Phe Gly Gly Gly Thr Lys Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
```

```
                165                 170                 175
Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
            195                 200                 205

His Arg Ser Tyr Ser Cys Gln Val Thr His Glu Gly Ser Thr Val Glu
        210                 215                 220

Lys Thr Val Ala Pro Ala Glu Cys Ser
225                 230
```

```
<210> SEQ ID NO 13
<211> LENGTH: 15
<212> TYPE: DNA
<213> ORGANISM: Homo sapiens
<220> FEATURE:
<221> NAME/KEY: CDS
<222> LOCATION: (1)..(15)

<400> SEQUENCE: 13 agc tat gct atc agc                                              15
Ser Tyr Ala Ile Ser
  1               5
```

```
<210> SEQ ID NO 14
<211> LENGTH: 5
<212> TYPE: PRT
<213> ORGANISM: Homo sapiens

<400> SEQUENCE: 14

Ser Tyr Ala Ile Ser
  1               5
```

```
<210> SEQ ID NO 15
<211> LENGTH: 51
<212> TYPE: DNA
<213> ORGANISM: Homo sapiens
<220> FEATURE:
<221> NAME/KEY: CDS
<222> LOCATION: (1)..(51)

<400> SEQUENCE: 15 ggg atc atc cct atc ttt ggt aca gca aac tac gca cag aag ttc cag   48
Gly Ile Ile Pro Ile Phe Gly Thr Ala Asn Tyr Ala Gln Lys Phe Gln
  1               5                  10                  15 ggc                                                              51
Gly
```

```
<210> SEQ ID NO 16
<211> LENGTH: 17
<212> TYPE: PRT
<213> ORGANISM: Homo sapiens

<400> SEQUENCE: 16

Gly Ile Ile Pro Ile Phe Gly Thr Ala Asn Tyr Ala Gln Lys Phe Gln
  1               5                  10                  15

Gly
```

```
<210> SEQ ID NO 17
<211> LENGTH: 63
<212> TYPE: DNA
<213> ORGANISM: Homo sapiens
<220> FEATURE:
<221> NAME/KEY: CDS
<222> LOCATION: (1)..(63)
```

-continued

```
<400> SEQUENCE: 17 gcg cca tta cga ttt ttg gag tgg tcc acc caa gac cac tac tac tac      48
Ala Pro Leu Arg Phe Leu Glu Trp Ser Thr Gln Asp His Tyr Tyr Tyr
 1               5                  10                  15 tac tac atg gac gtc                                                   63
Tyr Tyr Met Asp Val
             20

<210> SEQ ID NO 18
<211> LENGTH: 21
<212> TYPE: PRT
<213> ORGANISM: Homo sapiens

<400> SEQUENCE: 18

Ala Pro Leu Arg Phe Leu Glu Trp Ser Thr Gln Asp His Tyr Tyr Tyr
 1               5                  10                  15

Tyr Tyr Met Asp Val
             20

<210> SEQ ID NO 19
<211> LENGTH: 33
<212> TYPE: DNA
<213> ORGANISM: Homo sapiens
<220> FEATURE:
<221> NAME/KEY: CDS
<222> LOCATION: (1)..(33)

<400> SEQUENCE: 19 caa gga gac agc ctc aga agc tat tat gca agc                          33
Gln Gly Asp Ser Leu Arg Ser Tyr Tyr Ala Ser
 1               5                  10

<210> SEQ ID NO 20
<211> LENGTH: 11
<212> TYPE: PRT
<213> ORGANISM: Homo sapiens

<400> SEQUENCE: 20

Gln Gly Asp Ser Leu Arg Ser Tyr Tyr Ala Ser
 1               5                  10

<210> SEQ ID NO 21
<211> LENGTH: 21
<212> TYPE: DNA
<213> ORGANISM: Homo sapiens
<220> FEATURE:
<221> NAME/KEY: CDS
<222> LOCATION: (1)..(21)

<400> SEQUENCE: 21 ggt aaa aac aac cgg ccc tca                                          21
Gly Lys Asn Asn Arg Pro Ser
 1               5

<210> SEQ ID NO 22
<211> LENGTH: 7
<212> TYPE: PRT
<213> ORGANISM: Homo sapiens

<400> SEQUENCE: 22

Gly Lys Asn Asn Arg Pro Ser
 1               5

<210> SEQ ID NO 23
<211> LENGTH: 33
<212> TYPE: DNA
```

```
<213> ORGANISM: Homo sapiens
<220> FEATURE:
<221> NAME/KEY: CDS
<222> LOCATION: (1)..(33)

<400> SEQUENCE: 23 aac tcc cgg gac aac agt gat aac cgt ctg ata                    33
Asn Ser Arg Asp Asn Ser Asp Asn Arg Leu Ile
 1               5                  10

<210> SEQ ID NO 24
<211> LENGTH: 11
<212> TYPE: PRT
<213> ORGANISM: Homo sapiens

<400> SEQUENCE: 24

Asn Ser Arg Asp Asn Ser Asp Asn Arg Leu Ile
 1               5                  10

<210> SEQ ID NO 25
<211> LENGTH: 33
<212> TYPE: DNA
<213> ORGANISM: Homo sapiens
<220> FEATURE:
<221> NAME/KEY: CDS
<222> LOCATION: (1)..(33)

<400> SEQUENCE: 25 caa gga gac agc ctc aga agc tat tat gca acc                    33
Gln Gly Asp Ser Leu Arg Ser Tyr Tyr Ala Thr
 1               5                  10

<210> SEQ ID NO 26
<211> LENGTH: 11
<212> TYPE: PRT
<213> ORGANISM: Homo sapiens

<400> SEQUENCE: 26

Gln Gly Asp Ser Leu Arg Ser Tyr Tyr Ala Thr
 1               5                  10

<210> SEQ ID NO 27
<211> LENGTH: 21
<212> TYPE: DNA
<213> ORGANISM: Homo sapiens
<220> FEATURE:
<221> NAME/KEY: CDS
<222> LOCATION: (1)..(21)

<400> SEQUENCE: 27 ggt gaa aat aag cgg ccc tca                                    21
Gly Glu Asn Lys Arg Pro Ser
 1               5

<210> SEQ ID NO 28
<211> LENGTH: 7
<212> TYPE: PRT
<213> ORGANISM: Homo sapiens

<400> SEQUENCE: 28

Gly Glu Asn Lys Arg Pro Ser
 1               5

<210> SEQ ID NO 29
<211> LENGTH: 33
<212> TYPE: DNA
<213> ORGANISM: Homo sapiens
<220> FEATURE:
```

```
<221> NAME/KEY: CDS
<222> LOCATION: (1)..(33)

<400> SEQUENCE: 29 aaa tct cgg gat ggc agt ggt caa cat ctg gtg                    33
Lys Ser Arg Asp Gly Ser Gly Gln His Leu Val
 1               5                  10

<210> SEQ ID NO 30
<211> LENGTH: 11
<212> TYPE: PRT
<213> ORGANISM: Homo sapiens

<400> SEQUENCE: 30

Lys Ser Arg Asp Gly Ser Gly Gln His Leu Val
 1               5                  10

<210> SEQ ID NO 31
<211> LENGTH: 24
<212> TYPE: DNA
<213> ORGANISM: Homo sapiens
<220> FEATURE:
<221> NAME/KEY: CDS
<222> LOCATION: (1)..(24)

<400> SEQUENCE: 31 agc agt ggt gat tac tac tgg agt                                24
Ser Ser Gly Asp Tyr Tyr Trp Ser
 1               5

<210> SEQ ID NO 32
<211> LENGTH: 8
<212> TYPE: PRT
<213> ORGANISM: Homo sapiens

<400> SEQUENCE: 32

Ser Ser Gly Asp Tyr Tyr Trp Ser
 1               5

<210> SEQ ID NO 33
<211> LENGTH: 48
<212> TYPE: DNA
<213> ORGANISM: Homo sapiens
<220> FEATURE:
<221> NAME/KEY: CDS
<222> LOCATION: (1)..(48)

<400> SEQUENCE: 33 tac atc tat tac agt ggg agc acc gac tac aac ccg tcc ctc aag agt    48
Tyr Ile Tyr Tyr Ser Gly Ser Thr Asp Tyr Asn Pro Ser Leu Lys Ser
 1               5                  10                  15

<210> SEQ ID NO 34
<211> LENGTH: 16
<212> TYPE: PRT
<213> ORGANISM: Homo sapiens

<400> SEQUENCE: 34

Tyr Ile Tyr Tyr Ser Gly Ser Thr Asp Tyr Asn Pro Ser Leu Lys Ser
 1               5                  10                  15

<210> SEQ ID NO 35
<211> LENGTH: 33
<212> TYPE: DNA
<213> ORGANISM: Homo sapiens
<220> FEATURE:
<221> NAME/KEY: CDS
<222> LOCATION: (1)..(33)
```

```
<400> SEQUENCE: 35 gtg tcg att ttt gga gtg ggg aca ttt gac tac                              33
Val Ser Ile Phe Gly Val Gly Thr Phe Asp Tyr
 1               5                   10

<210> SEQ ID NO 36
<211> LENGTH: 11
<212> TYPE: PRT
<213> ORGANISM: Homo sapiens

<400> SEQUENCE: 36

Val Ser Ile Phe Gly Val Gly Thr Phe Asp Tyr
 1               5                   10

<210> SEQ ID NO 37
<211> LENGTH: 363
<212> TYPE: DNA
<213> ORGANISM: Homo sapiens
<220> FEATURE:
<221> NAME/KEY: CDS
<222> LOCATION: (1)..(363)

<400> SEQUENCE: 37 cag gtg cag ctg cag gag tcg ggc cca gga ctg gtg aag cct tca cag        48
Gln Val Gln Leu Gln Glu Ser Gly Pro Gly Leu Val Lys Pro Ser Gln
 1               5                   10                  15 acc ctg tcc ctc acc tgc act gtc tct ggt ggc tcc atc agc agt ggt        96
Thr Leu Ser Leu Thr Cys Thr Val Ser Gly Gly Ser Ile Ser Ser Gly
             20                  25                  30 gat tac tac tgg agt tgg atc cgc cag ccc cca ggg aag ggc ctg gag       144
Asp Tyr Tyr Trp Ser Trp Ile Arg Gln Pro Pro Gly Lys Gly Leu Glu
         35                  40                  45 tgg att ggg tac atc tat tac agt ggg agc acc gac tac aac ccg tcc       192
Trp Ile Gly Tyr Ile Tyr Tyr Ser Gly Ser Thr Asp Tyr Asn Pro Ser
     50                  55                  60 ctc aag agt cga gtc acc atg tcc gta gac acg tcc aag aat cag ttt       240
Leu Lys Ser Arg Val Thr Met Ser Val Asp Thr Ser Lys Asn Gln Phe
 65                  70                  75                  80 tcc ctg aag gtc aac tct gtg acc gcc gca gac acg gct gtg tat tac       288
Ser Leu Lys Val Asn Ser Val Thr Ala Ala Asp Thr Ala Val Tyr Tyr
                 85                  90                  95 tgt gcg aga gtg tcg att ttt gga gtg ggg aca ttt gac tac tgg ggc       336
Cys Ala Arg Val Ser Ile Phe Gly Val Gly Thr Phe Asp Tyr Trp Gly
            100                 105                 110 cag ggc acc ctg gtc acc gtc tca agc                                    363
Gln Gly Thr Leu Val Thr Val Ser Ser
        115                 120

<210> SEQ ID NO 38
<211> LENGTH: 121
<212> TYPE: PRT
<213> ORGANISM: Homo sapiens

<400> SEQUENCE: 38

Gln Val Gln Leu Gln Glu Ser Gly Pro Gly Leu Val Lys Pro Ser Gln
 1               5                   10                  15

Thr Leu Ser Leu Thr Cys Thr Val Ser Gly Gly Ser Ile Ser Ser Gly
             20                  25                  30

Asp Tyr Tyr Trp Ser Trp Ile Arg Gln Pro Pro Gly Lys Gly Leu Glu
         35                  40                  45

Trp Ile Gly Tyr Ile Tyr Tyr Ser Gly Ser Thr Asp Tyr Asn Pro Ser
     50                  55                  60
```

```
Leu Lys Ser Arg Val Thr Met Ser Val Asp Thr Ser Lys Asn Gln Phe
 65                  70                  75                  80

Ser Leu Lys Val Asn Ser Val Thr Ala Ala Asp Thr Ala Val Tyr Tyr
                 85                  90                  95

Cys Ala Arg Val Ser Ile Phe Gly Val Gly Thr Phe Asp Tyr Trp Gly
            100                 105                 110

Gln Gly Thr Leu Val Thr Val Ser Ser
        115                 120
```

<210> SEQ ID NO 39
<211> LENGTH: 30
<212> TYPE: DNA
<213> ORGANISM: Homo sapiens
<220> FEATURE:
<221> NAME/KEY: CDS
<222> LOCATION: (1)..(30)

<400> SEQUENCE: 39

```
agg gcc agt cag agt gtt agc agc tac tta                              30
Arg Ala Ser Gln Ser Val Ser Ser Tyr Leu
 1               5                  10
```

<210> SEQ ID NO 40
<211> LENGTH: 10
<212> TYPE: PRT
<213> ORGANISM: Homo sapiens

<400> SEQUENCE: 40

```
Arg Ala Ser Gln Ser Val Ser Ser Tyr Leu
 1               5                  10
```

<210> SEQ ID NO 41
<211> LENGTH: 21
<212> TYPE: DNA
<213> ORGANISM: Homo sapiens
<220> FEATURE:
<221> NAME/KEY: CDS
<222> LOCATION: (1)..(21)

<400> SEQUENCE: 41

```
gat gca tcc aac agg gcc act                                          21
Asp Ala Ser Asn Arg Ala Thr
 1               5
```

<210> SEQ ID NO 42
<211> LENGTH: 7
<212> TYPE: PRT
<213> ORGANISM: Homo sapiens

<400> SEQUENCE: 42

```
Asp Ala Ser Asn Arg Ala Thr
 1               5
```

<210> SEQ ID NO 43
<211> LENGTH: 24
<212> TYPE: DNA
<213> ORGANISM: Homo sapiens
<220> FEATURE:
<221> NAME/KEY: CDS
<222> LOCATION: (1)..(24)

<400> SEQUENCE: 43

```
cac cag tat ggt agc aca cct ctc                                      24
His Gln Tyr Gly Ser Thr Pro Leu
 1               5
```

<210> SEQ ID NO 44
<211> LENGTH: 8
<212> TYPE: PRT
<213> ORGANISM: Homo sapiens

<400> SEQUENCE: 44

His Gln Tyr Gly Ser Thr Pro Leu
 1               5

<210> SEQ ID NO 45
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 45

```
gaa att gtg atg aca cag tct cca gcc acc ctg tct ttg tct cca ggg        48
Glu Ile Val Met Thr Gln Ser Pro Ala Thr Leu Ser Leu Ser Pro Gly
 1               5                  10                  15 gaa aga gcc acc ctc tcc tgc agg gcc agt cag agt gtt agc agc tac        96
Glu Arg Ala Thr Leu Ser Cys Arg Ala Ser Gln Ser Val Ser Ser Tyr
             20                  25                  30 tta gcc tgg tac caa cag aaa cct ggc cag gct ccc agg ctc ctc atc       144
Leu Ala Trp Tyr Gln Gln Lys Pro Gly Gln Ala Pro Arg Leu Leu Ile
         35                  40                  45 tat gat gca tcc aac agg gcc act ggc atc cca gcc agg ttc agt ggc       192
Tyr Asp Ala Ser Asn Arg Ala Thr Gly Ile Pro Ala Arg Phe Ser Gly
     50                  55                  60 agt ggg tct ggg aca gac ttc act ctc acc atc agc agc cta gag cct       240
Ser Gly Ser Gly Thr Asp Phe Thr Leu Thr Ile Ser Ser Leu Glu Pro
 65                  70                  75                  80 gaa gat ttt gca gtg tat tac tgt cac cag tat ggt agc aca cct ctc       288
Glu Asp Phe Ala Val Tyr Tyr Cys His Gln Tyr Gly Ser Thr Pro Leu
                 85                  90                  95 act ttc ggc gga ggg acc aag gcg gag atc aaa                           321
Thr Phe Gly Gly Gly Thr Lys Ala Glu Ile Lys
            100                 105
```

<210> SEQ ID NO 46
<211> LENGTH: 107
<212> TYPE: PRT
<213> ORGANISM: Homo sapiens

<400> SEQUENCE: 46

Glu Ile Val Met Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys His Gln Tyr Gly Ser Thr Pro Leu
                 85                  90                  95

Thr Phe Gly Gly Gly Thr Lys Ala Glu Ile Lys
            100                 105

<210> SEQ ID NO 47
<211> LENGTH: 357
<212> TYPE: DNA
<213> ORGANISM: Mus musculus
<220> FEATURE:
<221> NAME/KEY: CDS
<222> LOCATION: (1)..(357)

<400> SEQUENCE: 47

| cag | gtg | cag | ctg | aag | cag | tca | gga | cct | ggc | cta | gtg | cag | ccc | tca | cag | 48 |
| Gln | Val | Gln | Leu | Lys | Gln | Ser | Gly | Pro | Gly | Leu | Val | Gln | Pro | Ser | Gln | |
| 1 | | | | 5 | | | | | 10 | | | | | 15 | | |

| agc | ctg | tcc | atc | acc | tgc | aca | gtc | tct | ggt | ttc | tca | tta | act | aac | tat | 96 |
| Ser | Leu | Ser | Ile | Thr | Cys | Thr | Val | Ser | Gly | Phe | Ser | Leu | Thr | Asn | Tyr | |
| | | | | 20 | | | | | 25 | | | | | 30 | | |

| ggt | gta | cac | tgg | gtt | cgc | cag | tct | cca | gga | aag | ggt | ctg | gag | tgg | ctg | 144 |
| Gly | Val | His | Trp | Val | Arg | Gln | Ser | Pro | Gly | Lys | Gly | Leu | Glu | Trp | Leu | |
| | | 35 | | | | | 40 | | | | | 45 | | | | |

| gga | gtg | ata | tgg | agt | ggt | gga | aac | aca | gac | tat | aat | aca | cct | ttc | aca | 192 |
| Gly | Val | Ile | Trp | Ser | Gly | Gly | Asn | Thr | Asp | Tyr | Asn | Thr | Pro | Phe | Thr | |
| 50 | | | | | 55 | | | | | 60 | | | | | | |

| tcc | aga | ctg | agc | atc | aac | aag | gac | aat | tcc | aag | agc | caa | gtt | ttc | ttt | 240 |
| Ser | Arg | Leu | Ser | Ile | Asn | Lys | Asp | Asn | Ser | Lys | Ser | Gln | Val | Phe | Phe | |
| 65 | | | | | 70 | | | | | 75 | | | | | 80 | |

| aaa | atg | aac | agt | ctg | caa | tct | aat | gac | aca | gcc | ata | tat | tac | tgt | gcc | 288 |
| Lys | Met | Asn | Ser | Leu | Gln | Ser | Asn | Asp | Thr | Ala | Ile | Tyr | Tyr | Cys | Ala | |
| | | | | 85 | | | | | 90 | | | | | 95 | | |

| aga | gcc | ctc | acc | tac | tat | gat | tac | gag | ttt | gct | tac | tgg | ggc | caa | ggg | 336 |
| Arg | Ala | Leu | Thr | Tyr | Tyr | Asp | Tyr | Glu | Phe | Ala | Tyr | Trp | Gly | Gln | Gly | |
| | | | 100 | | | | | 105 | | | | | 110 | | | |

| act | ctg | gtc | act | gtc | tct | gca | | | | | | | | | | 357 |
| Thr | Leu | Val | Thr | Val | Ser | Ala | | | | | | | | | | |
| | | 115 | | | | | | | | | | | | | | |

<210> SEQ ID NO 48
<211> LENGTH: 119
<212> TYPE: PRT
<213> ORGANISM: Mus musculus

<400> SEQUENCE: 48

| Gln | Val | Gln | Leu | Lys | Gln | Ser | Gly | Pro | Gly | Leu | Val | Gln | Pro | Ser | Gln |
| 1 | | | | 5 | | | | | 10 | | | | | 15 | |

| Ser | Leu | Ser | Ile | Thr | Cys | Thr | Val | Ser | Gly | Phe | Ser | Leu | Thr | Asn | Tyr |
| | | | | 20 | | | | | 25 | | | | | 30 | |

| Gly | Val | His | Trp | Val | Arg | Gln | Ser | Pro | Gly | Lys | Gly | Leu | Glu | Trp | Leu |
| | | 35 | | | | | 40 | | | | | 45 | | | |

| Gly | Val | Ile | Trp | Ser | Gly | Gly | Asn | Thr | Asp | Tyr | Asn | Thr | Pro | Phe | Thr |
| 50 | | | | | 55 | | | | | 60 | | | | | |

| Ser | Arg | Leu | Ser | Ile | Asn | Lys | Asp | Asn | Ser | Lys | Ser | Gln | Val | Phe | Phe |
| 65 | | | | | 70 | | | | | 75 | | | | | 80 |

| Lys | Met | Asn | Ser | Leu | Gln | Ser | Asn | Asp | Thr | Ala | Ile | Tyr | Tyr | Cys | Ala |
| | | | | 85 | | | | | 90 | | | | | 95 | |

| Arg | Ala | Leu | Thr | Tyr | Tyr | Asp | Tyr | Glu | Phe | Ala | Tyr | Trp | Gly | Gln | Gly |
| | | | 100 | | | | | 105 | | | | | 110 | | |

| Thr | Leu | Val | Thr | Val | Ser | Ala |
| | | 115 | | | | |

<210> SEQ ID NO 49
<211> LENGTH: 321
<212> TYPE: DNA
<213> ORGANISM: Mus musculus
<220> FEATURE:

```
<221> NAME/KEY: CDS
<222> LOCATION: (1)..(321)

<400> SEQUENCE: 49 gac atc ttg ctg act cag tct cca gtc atc ctg tct gtg agt cca gga      48
Asp Ile Leu Leu Thr Gln Ser Pro Val Ile Leu Ser Val Ser Pro Gly
 1               5                  10                  15 gaa aga gtc agt ttc tcc tgc agg gcc agt cag agt att ggc aca aac      96
Glu Arg Val Ser Phe Ser Cys Arg Ala Ser Gln Ser Ile Gly Thr Asn
             20                  25                  30 ata cac tgg tat cag caa aga aca aat ggt tct cca agg ctt ctc ata     144
Ile His Trp Tyr Gln Gln Arg Thr Asn Gly Ser Pro Arg Leu Leu Ile
         35                  40                  45 aag tat gct tct gag tct atc tct ggg atc cct tcc agg ttt agt ggc     192
Lys Tyr Ala Ser Glu Ser Ile Ser Gly Ile Pro Ser Arg Phe Ser Gly
     50                  55                  60 agt gga tca ggg aca gat ttt act ctt agc atc aac agt gtg gag tct     240
Ser Gly Ser Gly Thr Asp Phe Thr Leu Ser Ile Asn Ser Val Glu Ser
 65                  70                  75                  80 gaa gat att gca gat tat tac tgt caa caa aat aat aac tgg cca acc     288
Glu Asp Ile Ala Asp Tyr Tyr Cys Gln Gln Asn Asn Asn Trp Pro Thr
                 85                  90                  95 acg ttc ggt gct ggg acc aag ctg gag ctg aaa                         321
Thr Phe Gly Ala Gly Thr Lys Leu Glu Leu Lys
             100                 105

<210> SEQ ID NO 50
<211> LENGTH: 107
<212> TYPE: PRT
<213> ORGANISM: Mus musculus

<400> SEQUENCE: 50

Asp Ile Leu Leu Thr Gln Ser Pro Val Ile Leu Ser Val Ser Pro Gly
 1               5                  10                  15

Glu Arg Val Ser Phe Ser Cys Arg Ala Ser Gln Ser Ile Gly Thr Asn
             20                  25                  30

Ile His Trp Tyr Gln Gln Arg Thr Asn Gly Ser Pro Arg Leu Leu Ile
         35                  40                  45

Lys Tyr Ala Ser Glu Ser Ile Ser Gly Ile Pro Ser Arg Phe Ser Gly
     50                  55                  60

Ser Gly Ser Gly Thr Asp Phe Thr Leu Ser Ile Asn Ser Val Glu Ser
 65                  70                  75                  80

Glu Asp Ile Ala Asp Tyr Tyr Cys Gln Gln Asn Asn Asn Trp Pro Thr
                 85                  90                  95

Thr Phe Gly Ala Gly Thr Lys Leu Glu Leu Lys
             100                 105
```